(12) United States Patent
Wong et al.

(10) Patent No.: US 9,340,601 B2
(45) Date of Patent: May 17, 2016

(54) SPLICE VARIANTS OF THE EGF RECEPTOR

(75) Inventors: Albert J. Wong, Menlo Park, CA (US); Emily Piccione Griffin, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 2271 days.

(21) Appl. No.: 12/040,329

(22) Filed: Feb. 29, 2008

(65) Prior Publication Data

US 2009/0081222 A1    Mar. 26, 2009

Related U.S. Application Data

(60) Provisional application No. 60/904,498, filed on Mar. 1, 2007.

(51) Int. Cl.
 C07K 14/71   (2006.01)
 C07K 16/28   (2006.01)
 G01N 33/574  (2006.01)
 A61K 38/00   (2006.01)

(52) U.S. Cl.
 CPC ............. *C07K 14/71* (2013.01); *C07K 16/2863* (2013.01); *G01N 33/574* (2013.01); *A61K 38/00* (2013.01); *C07K 2317/34* (2013.01); *G01N 2500/10* (2013.01)

(58) Field of Classification Search
 None
 See application file for complete search history.

(56) References Cited

U.S. PATENT DOCUMENTS

| | | | |
|---|---|---|---|
| 5,212,290 A | 5/1993 | Vogelstein | |
| 5,401,828 A | 3/1995 | Vogelstein et al. | |
| 5,811,098 A * | 9/1998 | Plowman et al. | 424/178.1 |
| 5,837,821 A | 11/1998 | Wu et al. | |
| 6,071,891 A | 6/2000 | Low et al. | |
| 6,090,388 A | 7/2000 | Wang | |
| 6,224,868 B1 | 5/2001 | Wong et al. | |
| 6,455,498 B1 | 9/2002 | Vogelstein et al. | |
| 6,506,559 B1 | 1/2003 | Fire et al. | |
| 6,797,276 B1 | 9/2004 | Glenn et al. | |
| 7,628,986 B2 * | 12/2009 | Weber et al. | 424/130.1 |
| 2005/0100546 A1 | 5/2005 | Jakobovits et al. | |
| 2005/0222059 A1 | 10/2005 | Tang | |
| 2005/0272083 A1 | 12/2005 | Seshagiri | |
| 2006/0234343 A1 | 10/2006 | Ward | |

FOREIGN PATENT DOCUMENTS

| | | |
|---|---|---|
| WO | 2006091899 | 10/2006 |
| WO | 2006110478 | 10/2006 |

OTHER PUBLICATIONS

Albert J. Wong, et al., "Structural alterations of the epidermal growth factor receptor gene in human gliomas," Proc. Natl. Acad. Sci. USA, Apr. 1992, vol. 89, 2965-2969.
Emily Piccione, et al., "Identification of a novel epidermal growth factor receptor variant," Proc. Amer. Assoc. Cancer Res., 2006, vol. 47, Abstract #63.

* cited by examiner

*Primary Examiner* — Alana Harris Dent
(74) *Attorney, Agent, or Firm* — Bozicevic, Field & Francis LLP; David J. Aston

(57) ABSTRACT

The present invention relates to a novel form of human EGFR found in certain tumors and conditions. The protein is termed here mLEEK, and the cDNA that encodes it has also been isolated. The mLEEK protein is capable of efficiently inducing the transcription of multiple genes resulting in various physiologic processes. Antibodies directed against the protein can be used for improving the diagnosis of diseases or for the treatment of diseases. The protein itself can be directly used or blocked for therapeutic purposes. Nucleic acid based probes or PCR primers specific for the mLEEK sequence can be used for diagnostic purposes. Inhibitory nucleic acid based molecules, such as antisense, siRNA, or shRNA, may be used for therapeutic purposes. The mLEEK sequence is essentially formed by the skipping of exons 2 through 22 in the EGF receptor gene leading to a fusion of exon 1 to exon 23. Other mutants are disclosed, which include the fusion of exon 1 to exon 24 and the fusion of exons 1 to exon 28.

6 Claims, 14 Drawing Sheets

Splice Variant Structure for mLEEK (1:23 fusion)

| Exon 1 | | | | | / = exon 1/exon 2 border at nt 274 | Exon 2... | | | Exon 22/exon 23 border at / bold G precedes nt 2888 | | | | | | | |
|---|---|---|---|---|---|---|---|---|---|---|---|---|---|---|---|---|
| Leu | Glu- | Glu- | Lys- | Lys- | Val- | Cys- | Gln | ... | Ser- | Tyr- | Gly- | Val- | Thr- | Val- | Trp- | Glu- | Leu |
| CTG | GAG | GAA | AAG | AAA | G/TT | TGC | CAA | ... | AGC | TAC | G/GG | GTG | ACC | GTT | TGG | GAG | TTG |

| CTG | GAG | GAA | AAG | AAA | splice | | | | GGG | GTG | ACC | GTT | TGG | GAG | TTG |

Final Sequence:

CTG GAG GAA AAG AAA GGC TGG ATG ATA GAC GCA GAT
L    E    E    K    K    <u>G</u>    V    T    V    W    E    L

Figure 1A

Splice Variant Structure for 1:24 fusion

| Exon 1 | | | | | / = exon 1/exon 2 border at nt 274 | Exon 2... | | | Exon 23/exon 24 border at / bold G precedes nt 3035 | | | | | | | |
|---|---|---|---|---|---|---|---|---|---|---|---|---|---|---|---|---|
| Leu | Glu- | Glu- | Lys- | Lys- | Val- | Cys- | Gln | ... | Gly- | Gln- | Cys- | Trp- | Met- | Ile- | Asp- | Ala- | Asp |
| CTG | GAG | GAA | AAG | AAA | G/TT | TGC | CAA | ... | GGT | CAA | T/GC | TGG | ATG | ATA | GAC | GCA | GAT |
| CTG | GAG | GAA | AAG | AAA | | splice | | | GGC | TGG | ATG | ATA | GAC | GCA | GAT | | |

Final Sequence:

CTG GAG GAA AAG AAA GGC TGG ATG ATA GAC GCA GAT
  L   E   E   K   K   <u>G</u>   W   M   I   D   A   D

Figure 1B

Splice Variant Structure for 1:28 fusion

| Exon 1 | | | | | / = exon 1/exon 2 border at nt 274 | Exon 2... | | | Exon 27/exon 28 border at / bold G precedes nt 3458 | | | | | | |
|---|---|---|---|---|---|---|---|---|---|---|---|---|---|---|---|
| Leu | Glu- | Glu- | Lys- | Lys- | Val- | Cys- | Gln | ... | Val- | Pro- | Glu- | Tyr- | Ile- | Asn- | Gln- | Ser- | Val- |
| CTG | GAG | GAA | AAG | AAA | G/TT | TGC | CAA | ... | GTG | CCT | G/AA | TAC | ATA | AAC | CAG | TCC | GTT |
| CTG | GAG | GAA | AAG | AAA | | splice | | | GAA | TAC | ATA | AAC | CAG | TCC | GTT |

Final Sequence:

CTG GAG GAA AAG AAA GAA TAC ATA AAC CAG TCC GTT
 L    E    E    K    K    E    Y    I    N    Q    S    V

Figure 1C

5A
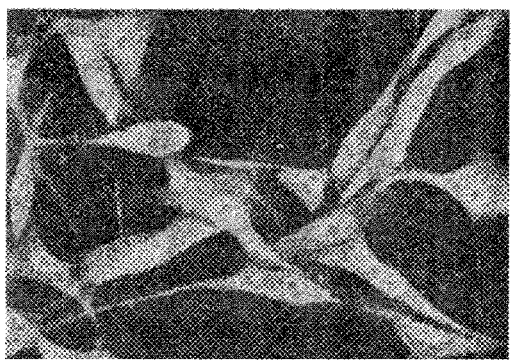
anti-mLeek
5B
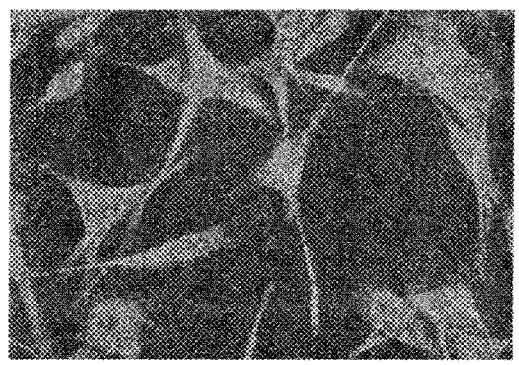
preimmune
5C
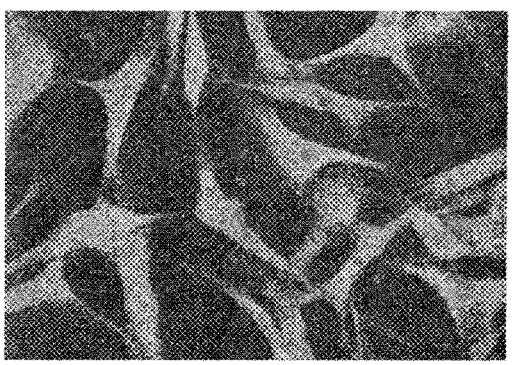
anti-mLeek
+ immunizing peptide
5D
anti-mLeek
+ nonspecific peptide
Figure 5A-D

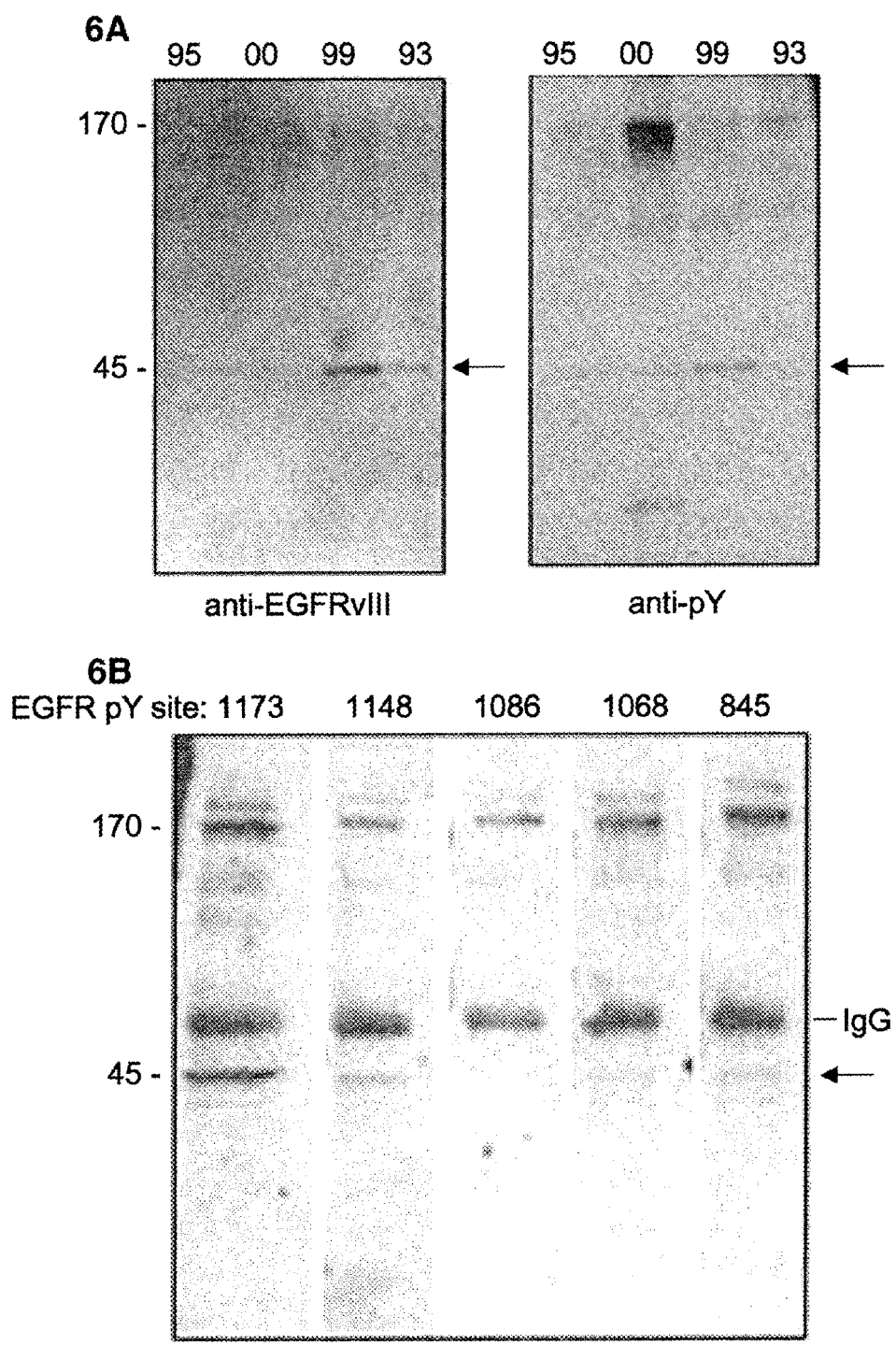
Figure 6A-B

13A
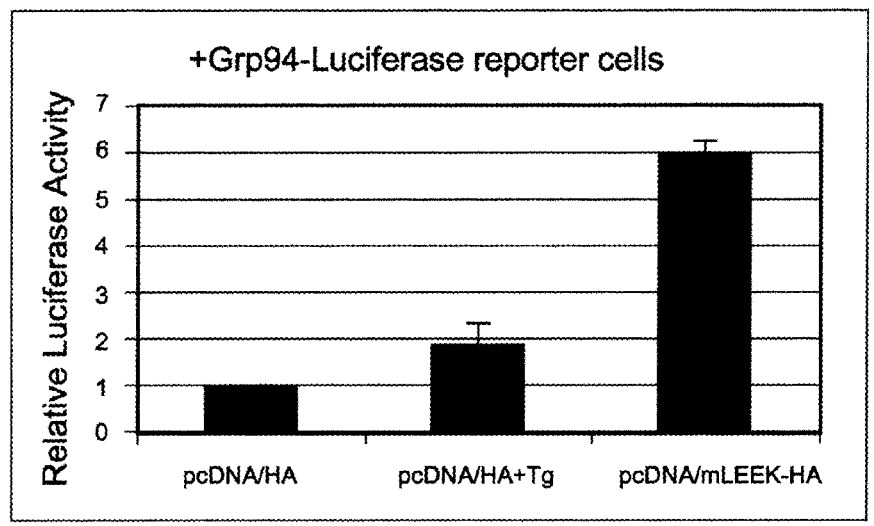
13B
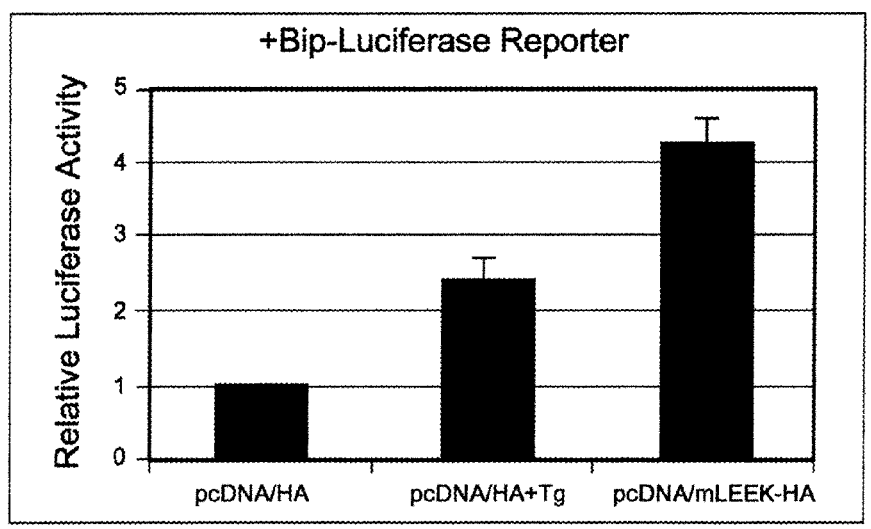
Figure 13

SPLICE VARIANTS OF THE EGF RECEPTOR

CROSS-REFERENCE TO RELATED APPLICATIONS

This application claims priority from U.S. Provisional Patent Application No. 60/904,498 filed on Mar. 1, 2007, which is hereby incorporated by reference in its entirety.

STATEMENT OF GOVERNMENTAL SUPPORT

This invention was made with U.S. Government support under contracts CA069495 and CA096539 awarded by the National Institutes of Health. The Government has certain rights in this invention.

REFERENCE TO SEQUENCE LISTING, COMPUTER PROGRAM, OR COMPACT DISK

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Field of the Invention

The present invention relates to the field of cellular growth factor receptors, particularly to novel forms of epidermal growth factor receptor (EGFR), involving deletions, to molecular techniques for analyzing and producing the novel forms of EGFR, to other compositions relating to the novel proteins and genetic constructs encoding same, and to potential uses of the constructs.

2. Related Art

The epidermal growth factor receptor, or EGF receptor, is a transmembrane receptor protein that binds epidermal growth factor (EGF). Following the binding of EGF, the intrinsic tyrosine kinase activity of the receptor is activated, which leads to the phosphorylation of numerous substrates. The signaling cascade that is initiated has a significant role in driving cells to divide. The EGF receptor is also known to be involved in enhancing cell motility, invasiveness and survival among many other phenotypes. There is increased expression of the protein in numerous types of cancers, and overexpression has been shown to enhance the tumorigenic properties of cancer cells as well as to transform normal cells into cancer cells. For these reasons, the EGF receptor has been a target for several anti-cancer therapies. Two small molecule inhibitors of the tyrosine kinase activity of the receptor have received FDA approval and are now marketed as therapies for several cancers including non-small cell carcinoma of the lung. Antibodies directed against the EGF receptor have also been approved by the FDA as anti-cancer therapeutics.

On the other hand, stimulation of the EGF receptor can actually be beneficial in some cases. For example, in skin wounds the application of EGF can promote healing.

Several variant forms of the EGF receptor have been described. The most common alteration is known as EGF receptor variant III, or EGFRvIII. This represents the skipping of exons 2 through 7 resulting in the fusion of exon 1 to exon 8. The amino acid sequence represents the joining of amino acid 5 of the mature protein to amino acid 274 and the generation of a unique glycine at the junction. The protein alteration is characterized by the amino acid sequence LEEKKGNYVVTDH, (SEQ ID NO: 1) where the underlined G represents the glycine created at the fusion junction. The "mature form" lacks the first 25 amino acids found in the pro peptide and begins with a leucine, as can be seen in the sequences disclosed. Its full length would therefore not include the signal sequence, would include substantially all of the peptide to the carboxy terminus.

There are also mutations within the EGF receptor sequence that either alter single amino acids or delete small regions of the protein. These alterations have been found to enhance sensitivity of the EGF receptor to small molecule tyrosine kinase inhibitors and their presence can reasonably predict patient response to these drugs.

While the membrane localization of the EGF receptor appears critical to some cellular functions, other intracellular localizations of the receptor have been described that also have some role in cell physiology. The EGF receptor has been found in the Golgi and endoplasmic reticulum where it is thought that the signals generated by the receptor in these compartments are relevant to cell growth and perhaps oncogenesis. More interestingly, immunohistochemical studies with antibodies directed against the EGF receptor have consistently identified reactivity in the nucleus in some normal physiologic states but especially in human cancer tissues such as breast and thyroid cancer. However, the nuclear localization was only found using antibodies directed against the intracytoplasmic domain and was not seen with antibodies against the extracellular domain. In vitro studies have found that the intact EGF receptor can translocate to the nucleus, either using an intrinsic nuclear localization signal or a sec translocon accessory protein that mediates nuclear transport. This nuclearly localized receptor is capable of activating the transcription of several genes involved in cell growth and the promotion of the cell cycle. It has further been shown that the EGF receptor can either bind directly or indirectly to the promoter region of these transcription factors, thus directly participating in the initiation of transcription. Intriguingly, a synthetic molecule that represents the intracytoplasmic domain of the receptor has a higher efficiency of nuclear translocation and activation of transcription factors.

The human epidermal growth factor receptor (EGFR) is identified as NCBI Gene EGFR. The full length DNA sequence referenced here is found at X00588. Additional full length EGFR sequence information is also publicly known, e.g., NM_005228. EGFR isoforms a, b, c and d have been reported.

SPECIFIC PATENTS AND PUBLICATIONS (WO/2006/091899), Epidermal Growth Factor Receptor Mutations, assigned to Amgen, Inc., inventors Freemen et al., discloses epidermal growth factor receptor ("EGFR") mutations and polynucleotides encoding mutant EGFR polypeptides in EGFR exons 18, 19, 20, 21, and 23.

United States Patent Application 2006/0234343 to Ward et al., published Oct. 19, 2006, entitled "Truncated EGF receptor," discloses a truncated epidermal growth factor receptor (EGFR) ectodomain comprising at least residues 1-492 of ErbB1 or equivalent residues of another member of the EGFR family.

United States Patent Application Publication Pub. No.: US 2005/0272083 A1 to Seshagiri published Dec. 8, 2005, entitled "EGFR mutations" discloses mutations in exons 18-21 of EGFR whereby the presence of a mutated EGFR gene or mutated EGFR protein indicates that the tumor is susceptible to treatment.

WO 2006/110478, "Mutations and polymorphisms of epidermal growth factor receptor," assigned to Novartis AG, by Culver, Kenneth, et al., discloses EGFR mutant and polymorphic polynucleotides and/or EGFR mutant/polymorphic polypeptides. This published application contains a chart containing information about previously-known and newly-identified mutations in the EGFR gene. However, these mutations are not in exons 1 or 23 on.

U.S. Pat. No. 6,455,498 Vogelstein, et al., issued Sep. 24, 2002, entitled "Structural alterations of the EGF receptor genes in human tumors," discloses immunogenic peptides having the sequence LEEKKGNYVVT (SEQ ID NO: 2) and LEEKKGNYVVTDHC (SEQ ID NO: 3). This is known as the variant 3, or vIII, splice variant. EGFRvIII is highly tumor specific as almost no normal tissue expresses this protein, but it is found to be present in a high percentage of human solid tumors including those from the breast, lung, colon, ovary and prostate. It has been shown that this protein does not bind EGF but is constitutively active. Overexpression of EGFRvIII will cause the transformation of cells. Various types of therapies directed against EGFRvIII have been explored including monoclonal antibodies and peptide vaccines directed against the fusion junction in the protein. PCR primer sets that selectively amplify the EGFRvIII alteration from tumor cDNA and antibodies specific for EGFRvIII which do not recognize normal EGF receptors, have been useful for determining patient prognosis. Indeed, it has been found that the presence of EGFRvIII predicts the response of glioblastoma patients to EGF receptor tyrosine kinase inhibitors.

Piccione et al., Proc. Am. Assoc. Canc. Res. Abstract from 2006 available Mar. 3, 2006 discloses certain aspects of one of the present novel EGFR splice variants.

Nicholas et al., "Epidermal Growth Factor Receptor-Mediated Signal Transduction in the Development and Therapy of Gliomas," *Clinical Cancer Research*, Vol. 12, 7261-7270, Dec. 15, 2006, provides a review of previously known EGFR splice variants, which differ from the ones now considered.

BRIEF SUMMARY OF THE INVENTION

The following brief summary is not intended to include all features and aspects of the present invention, nor does it imply that the invention must include all features and aspects discussed in this summary.

The present invention comprises, in certain aspects, an isolated polynucleotide that encodes an mLEEK polypeptide, which has an exon 1 to 23 fusion, or a structurally related polypeptide that contains a 1:24 exon fusion or a 1:28 exon fusion. These may have a sequence substantially identical to either SEQ ID NO: 4 (1:23 fusion, aka mLEEK), SEQ ID NO: 6 (1:24 fusion) or SEQ ID NO: 8 (1:28 fusion), respectively, in the case of the polynucleotides encoding the EGFR fusion propeptides. Alternatively, the polynucleotides may have a sequence substantially identical to SEQ ID NO: 4, SEQ ID NO: 6, or SEQ ID NO: 8, but lacking the first 207 nucleotides, to encode the mature truncated fusion EGFR polypeptides. The isolated polynucleotide may exist as synthetic DNA or RNA, or be transcribed as mRNA. Included in the invention are nucleic acids that specifically hybridize to these polynucleotides. More specifically, the hybridizing nucleic acids may comprise a primer, a probe, or combinations thereof. In addition, RNAi reagents may be designed to silence the RNA from cells expressing the mutant mRNAs disclosed. (Mutants here refer to mLEEK, exon 1:24 fusion and 1:28 fusion). A preferred molecule is shRNA specifically silencing mLEEK, exon 1:24 mutant or exon 1:28 mutant.

The present invention includes, in other aspects, an isolated polypeptide as encoded by one of the polynucleotides described above. The polypeptide may be expressed from one of the above polynucleotides, from codon variants, or may be made synthetically. Generally the present full length mutant polypeptides will have an extracellular domain less than about 30 amino acids, have a cytoplasmic autophosphorylation domain, and be substantially identical to the amino acid sequence of either SEQ ID NO: 5 (1:23 fusion, aka mLEEK), SEQ ID NO: 7 (1:24 fusion) or SEQ ID NO: 9 (1:28 fusion), respectively. The present polypeptides include both the mature forms and the signal peptide-bearing forms. (The mature forms lack the first 24 amino acids of SEQ IDs 5, 7, and 9). In general, substantial identity is based on the relatedness of the sequences as disclosed herein, but the invention may be regarded as including sequences that are at least 80% identical, 90% identical, 95% identical or 99% identical.

The present invention includes, in certain aspects, short peptides that encompass the novel fusion regions. These peptides may be used for immunization. The invention includes an isolated mutant peptide which is less than 50 amino acids in length, said peptide bearing a mutation of EGFR, said mutation being characterized by including the sequence (a) EEKKXVTV (1:23) (SEQ ID NO: 35), (b) LEEKKXWMI-DADSR (1:24) (SEQ ID NO: 10) or (c) LEEKKEYINQSVP (1:28) (SEQ ID NO: 11) where X is any amino acid or no amino acid, preferably G. These sequences represent the fusions of the respective exons, as explained in detail below. In order to extend the sequence, one may refer to the native sequence. In mLEEK, this sequence would be, e.g., MRPSG TAGAAL LALLA LCPAS RAL<u>EEKKXVTV</u>WEL MTFGS KPYDG IPASE ISSIL EKG (SEQ ID NO: 12), where the sequence given in (a) above is underlined. The isolated peptide must be long enough to be unambiguous with respect to other proteins. For example, it may be at least 5 amino acids in length, or 9-15 amino acids in length. The peptide may be characterized as a mutation of EGFR involving a splice variation, where the variation involves a splice between exon 1 and either exon 23, 28 or 24, and further characterized by having amino acids including those encoded at the splice junction. That is, the present peptides may be characterized as an EGFR peptide which is less than 50 amino acids in length, said peptide bearing a splice mutation of EGFR, said mutation being characterized by including the sequence KKXVT (exon 1:23) (SEQ ID NO: 36), KKEYI (exon 1:28) (SEQ ID NO: 37) or KKXWM (exon 1:24) (SEQ ID NO: 38), where X is preferably G.

The peptide may be used for immunization, in order to raise antibodies to the mutant protein, which antibodies may have an effect on the protein, or may be harvested for further use. The peptide may be coupled to adjuvants, or carriers, i.e., in an immunogenic formulation.

The formulation may be buffered and otherwise formulated for immunization of a mammal. The peptides may be formulated for various types of administration. The peptides can be administered orally, parenterally, intrathecally, topically, intravenously, intramuscularly or intradermally/epineurally. A preferred route of administration is subcutaneously or intramuscularly, for purposes of immunization.

The above-described mutant-encoding polynucleotides may be inserted into a vector and fused with other sequences, or placed under the control of various promoters. The vector is inserted into various host cells.

In certain aspects, the present invention comprises an antibody specific for the isolated peptide of the present mutants. This antibody may be a polyclonal antibody, either as antiserum or further purified. It may also be a monoclonal antibody or otherwise engineered antibody. The antibody may be designed to recognize the mutant in its active, i.e., phosphorylated form, which includes phosphorylated tyrosine residues, such as Y1173, Y1148, Y1086, Y1068 and Y992, which may or may not be phosphorylated in the mutant protein, depending on its activation status.

In other aspects, the present invention includes a method for diagnosing a tumorgenic phenotype in a sample isolated from a patient, wherein the sample is suspected of being cancerous, which method comprises: determining the presence in said sample of a nucleic acid encoding a mutant polypeptide; and identifying said sample as tumorigenic if the nucleic acid is determined to be present. The presence of the nucleic acid may be determined by nucleic acid probe or PCR primers. The sample may contain glial, breast, colon, gastric or ovarian cells. The sequences used will reflect the unique junction sequences disclosed below.

The present diagnostic methods may also be antibody based. One may test for the presence of an EGFR mutant protein, as opposed to a full length EGFR protein, by employing antibodies immunoreactive with mutant protein but not immunoreactive with intact EGFR protein. Since it has been shown that mLEEK is secreted or shed, the testing may be done on mutant polypeptide in serum.

In certain aspects, the present invention comprises a method of treating a tumor in a patient, based on interference with mutant expression or signaling. One may administer to a patient with a tumor a therapeutically effective amount of an antibody coupled to a therapeutic agent, said antibody specifically binding to a mutant EGFR protein but not specifically binding to an intact EGFR protein. The antibody may be coupled to a cytotoxic agent, such as a cell toxin (e.g., ricin A, pseudomonas exotoxin, or diphtheria toxin); or a radionuclide. In order to induce an appropriate immune response, the antibody should mimic a human protein, e.g., comprise only human antibody peptide sequences. That is, the present invention provides means for treating tumors in the sense of preventing their growth or the formation of a tumor from cells initially expressing the mutant EGFR receptor. The term "treatment" does not necessarily mean cure, but rather reduction in size or other undesirable properties, as is known in the art.

In other aspects, the present invention includes a method for diagnosing a disease in a patient, wherein the disease is characterized by the endoplasmic reticulum stress response. Such diseases include, but are not limited to, diabetes, cancer, cystic fibrosis, neurodegenerative disorders such as Alzheimer's, Huntington's and Parkinson's disease, and conditions of ischemia or hypoxia such as stroke or ischemic heart disease. The method comprises: determining the presence in a sample from a patient of a nucleic acid encoding a mutant polypeptide; and identifying said sample as containing a disease characterized by the endoplasmic reticulum stress response if the nucleic acid is determined to be present. The presence of the nucleic acid may be determined by nucleic acid probe or PCR primers. The sample may contain glial, breast, colon, gastric or ovarian cells. The sequences used will reflect the unique junction sequences disclosed below.

The present diagnostic methods may also be antibody based. One may test for the presence of an EGFR mutant protein, as opposed to a full length EGFR protein, by employing antibodies immunoreactive with mutant protein but not immunoreactive with intact EGFR protein. Since it has been shown that mLEEK is secreted or shed, the testing may be done on mutant polypeptide in serum.

In certain aspects, the present invention comprises a method of treating a disease characterized by the endoplasmic reticulum stress response in a patient, based on interference with mutant expression or signaling. One may administer to a patient with such a disease a therapeutically effective amount of an antibody coupled to a therapeutic agent, said antibody specifically binding to a mutant EGFR protein but not binding to an intact EGFR protein. The antibody may be coupled to a cytotoxic agent, such as a cell toxin (e.g., ricin A, pseudomonas exotoxin, or diphtheria toxin); or a radionuclide. In order to induce an appropriate immune response, the antibody should mimic a human protein, e.g., comprise only human antibody peptide sequences. The treatment of disease by reduction of the endoplasmic reticulum stress response in a cell may be brought about by means such as are known in the art, given the present disclosure of the role of the mutant EGFR in this stress response. For example, the mutant EGFR may be blocked by antibodies, or at the nucleic acid level. That is, one may inhibit mutant EGFR expression by antisense, siRNA molecules, or other agents. A preferred such agent is an agent which inhibits transcription or translation of the mutant EGFR polypeptide, preferably inhibiting the mLEEK polypeptide.

In certain aspects, the present invention comprises a kit for detecting an EGFR mutation involving an exon 1:23, 1:24 or 1:28 fusion, comprising: a pair of nucleic acid primers for amplification of a nucleotide sequence containing a deletion junction found in RNA of cells having an EGFR mutation, said pair of PCR primers including a first primer which comprises a sequence of contiguous wild-type EGFR nucleotides which are 5' to said deletion junction and a second primer which comprises a sequence of contiguous wild-type EGFR nucleotides which are 3' to said deletion junction; and a nucleotide probe comprising a sequence which is a complimentary to a sequence encoding a mutant peptide.

BRIEF DESCRIPTION OF THE DRAWINGS

FIGS. 1A, 1B and 1C are diagrams of the form of the sequence of mLEEK (FIG. 1A), the 1:24 Fusion (FIG. 1B), and the 1:28 fusion (FIG. 1C). In FIG. 1A, a 2613-base-pair in-frame EGFR deletion (upper) results in the fusion of normally distant EGFR gene and protein sequences (lower). A glycine residue is created at the fusion point. Numbers 274 and 2888 refer to the EGFR cDNA nucleotides flanking the deleted area. Similarly, in FIG. 1B, a fusion at the exon 23/24 border results in the joining of nucleotides 274 to 3035 and amino acids 25 to 91 (as counted in the intact protein). In FIG. 1C, a fusion at the exon 27/28 border results in the joining of nucleotides 274 to 3458 and amino acids 25 to 1091 (intact protein). Note that there are 24 fewer amino acids in the mature (cleaved) protein.

FIG. 5A through D is a series of four photographs showing immunofluorescence analysis of the distribution of mLEEK in U87MG cells. Original photographs showed green fluorescence against a black background. Subcellular localization of mLEEK in U87MG cells was visualized by indirect immunofluorescence with mLEEK polyclonal antibody followed by FITC-conjugated anti-rabbit secondary antibody (FIG. 5A). Cells were stained with preimmune serum as a negative control (FIG. 5B). As a further set of controls, the anti-mLEEK antibody was preincubated with either the immunizing peptide (FIG. 5C) or a non-specific peptide (FIG. 5D) and then used for immunofluorescence. Stain is seen predominantly in the nucleus. Controls 5B and 5C do not reveal distinct nuclear staining.

FIGS. 6A and B are photographs of Western blots showing identification of mLEEK and its phosphorylation in vivo. Arrows show 45 kD band.

FIGS. 13 A and B are graphs showing induction of transcription by mLEEK from the Grp94 (glucose regulated protein) promoter (13A) and the Grp/BiP promoter (13B) driving expression of luciferase reporter as compared to control plasmid expressing HA tag alone (pcDNA/HA).

DETAILED DESCRIPTION OF THE PREFERRED EMBODIMENT

Overview

Figure 2:
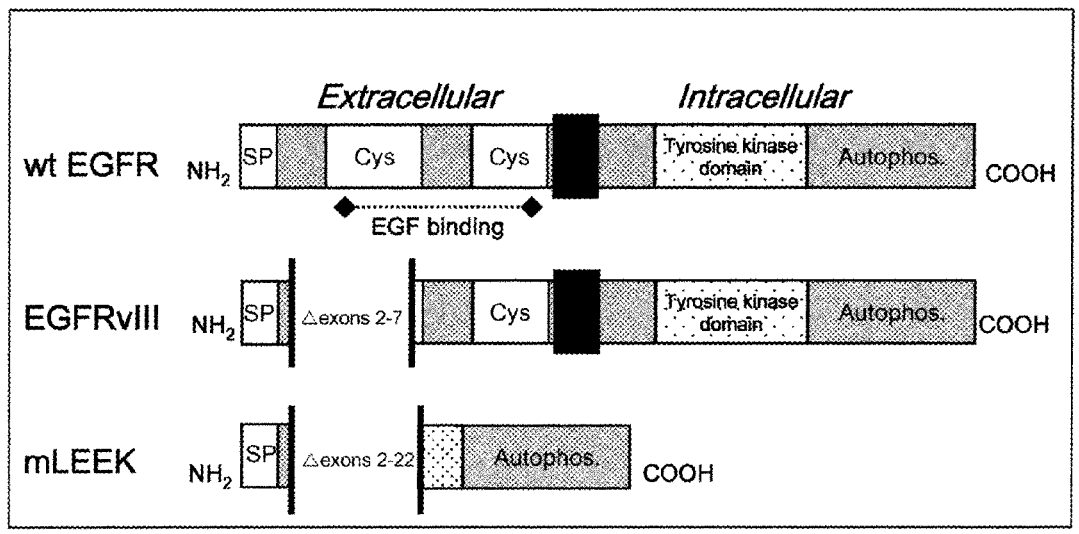
FIG. 2 is a diagram of the protein structure of wt EGFR and mutant forms. NH$_2$ refers to amino terminus; COOH refers to carboxyl terminus; TM refers to transmembrane segment; Autophos. refers to a domain with tyrosine residues for autophosphorylation; Cys refers to a cysteine-rich region; SP refers to a signal peptide.

The present invention relates to novel forms of human EGFR found in certain tumors. In one embodiment, the novel form is a fusion of the first exon to the 23$^{rd}$ exon of the EGFR, and is termed here mLEEK. The present invention includes both the cDNA that encodes the mLEEK polypeptide and the mLEEK polypeptide itself. The mLEEK polypeptide may be directly used for therapeutic purposes. The present invention also includes antibodies directed against the mLEEK protein, which can be used for improving the diagnosis of diseases or for the treatment of diseases. Also included in the present invention are nucleic acid based probes or PCR primers specific for the mLEEK nucleotide sequence, which may be used for diagnostic purposes. Inhibitory nucleic acid based molecules, such as antisense, siRNA, or shRNA, are also included in the present invention, and may be used for therapeutic purposes.

The mLEEK sequence is essentially formed by the skipping of exons 2 through 22 in the EGF receptor gene leading to a fusion of exon 1 to exon 23. The amino acid sequence represents the joining of amino acid 5 of the mature protein (i.e., following cleavage of the signal peptide) to amino acid 878 with the creation of a novel glycine at the junction. The protein alteration is characterized by the amino acid sequence LEEKK<u>G</u>VTVWEL, (SEQ ID NO: 13) where the underlined G represents the glycine created at the fusion junction. The present invention also includes exon fusions other than the 1:23 fusion. Specifically, the invention includes polynucleotides and proteins having sequences derived from the fusion of exons 1:24 and exons 1:28. The N-terminal region of these mutants contains the LEEK sequence, and these mutants are termed here mutant 1:24 and mutant 1:28. Also included are nucleic based probes or PCR primers specific for the 1:24 mutant or the 1:28 mutant polynucleotides; antibodies against the 1:24 mutant or 1:24 mutant polypeptides; and inhibitory nucleic acid based molecules specific fore the 1:23 or 1:24 mutant polynucleotides.

Thus, the mLEEK amino acid sequence may be represented as follows, where the full length EGFR sequence is included for reference:

(SEQ ID NO: 14)
MRPSGTAGAALLALLAALCPASRALEEKK

[[VCQGTSNKLTQLGTFEDHFLSLQRMFNNCEVVLGNLEITYVQRNYDLS

FLKTIQEVAGYVLIALNTVERIPLENLQIIRGNMYYENSYALAVLSNYDA

NKTGLKELPMRNLQEILHGAVRFSNNPALCNVESIQWRDIVSSDFLSNMS

MDFQNHLGSCQKCDPSCPNGSCWGAGEENCQKLTKIICAQQCSGRCRGKS

PSDCCHNQCAAGCTGPRESDCLVCRKFRDEATCKDTCPPLMLYNPTTYQM

DVNPEGKYSFGATCVKKCPR]] ((NYVVTDHGSCVRACGADSYEMEEDG

VRKCKKCEGPCRKVCNGIGIGEFKDSLSINATNIKHFKNCTSISGDLHIL

PVAFRGDSFTHTPPLDPQELDILKTVKEITGFLLIQAWPENRTDLHAFEN

LEIIRGRTKQHGQFSLAVVSLNITSLGLRSLKEISDGDVIISGNKNLCYA

NTINWKKLFGTSGQKTKIISNRGENSCKATGQVCHALCSPEGCWGPEPRD

CVSCRNVSRGRECVDKCNLLEGEPREFVENSECIQCHPECLPQAMNITCT

GRGPDNCIQCAHYIDGPHCVKTCPAGVMGENNTLVWKYADAGHVCHLCHP

NCTYGCTGPGLEGCPTNGPKIPSIATGMVGALLLLLVVALGIGLFMRRRH

IVRKRTLRRLLQERELVEPLTPSGEAPNQALLRILKETEFKKIKVLGSGA

FGTVYKGLWIPEGEKVKIPVAIKELREATSPKANKEILDEAYVMASVDNP

HVCRLLGICLTSTVQLITQLMPFGCLLDYVREHKDNIGSQYLLNWCVQIA

KGMNYLEDRRLVHRDLAARNVLVKTPQHVKITDFGLAKLLGAEEKEYHAE

GGKVPIKWMALESILHRIYTHQSDVWSY))

GVTVWELMTFGSKPYDGIPASEISSILEKGERLPQPPICTIDVYMIMVK

CWMIDADSRPKFRELIIEFSKMARDPQRYLVIQGDERMHLPSPTDSNFY

```
                       -continued
RALMDEEDMDDVVDADEYLIPQQGFFSSPSTSRTPLLSSLSATSNNSTV

ACIDRNGLQSCPIKEDSFLQRYSSDPTGALTEDSIDDTFLPVPEYINQS

VPKRPAGSVQNPVYHNQPLNPAPSRDPHYQDPHSTAVGNPEYLNTVQPT

CVNSTFDSPAHWAQKGSHQISLDNPDYQQDFFPKEAKPNGIFKGSTAEN

AEYLRVAPQSSEFIGA
```

The middle portion is set forth for reference purposes only. In mLEEK the underlined amino acids indicate where the exon sequences are joined. The sequences between the brackets, i.e., [[to]] are omitted in prior art variant 3, that is, amino acids 6-273 in the native sequence. The amino acids between the parentheses, ((to)) are also omitted in the present sequence, that is amino acids 6-877. The bolded and underlined sequences correspond to the representation in FIG. 1A and SEQ ID NO: 13.

For further illustration, EGFR isoform a (NP_005219) is shown below in the form of the present mLEEK:

```
                                              (SEQ ID NO: 15)
  1 MRPSGTAGAA LLALLAALCP ASRALEEKKV CQGTSNKLTQ
    LGTFEDHFLS LQRMFNNCEV

61 VLGNLEITYV QRNYDLSFLK TIQEVAGYVL IALNTVERIP
    LENLQIIRGN MYYENSYALA

121 VLSNYDANKT GLKELPMRNL QEILHGAVRF SNNPALCNVE
    SIQWRDIVSS DFLSNMSMDF

181 QNHLGSCQKC DPSCPNGSCW GAGEENCQKL TKIICAQQCS
    GRCRGKSPSD CCHNQCAAGC

241 TGPRESDCLV CRKFRDEATC KDTCPPLMLY NPTTYQMDVN
    PEGKYSFGAT CVKKCPRNYV

301 VTDHGSCVRA CGADSYEMEE DGVRKCKKCE GPCRKVCNGI
    GIGEFKDSLS INATNIKHFK

-continued
361 NCTSISGDLH ILPVAFRGDS FTHTPPLDPQ ELDILKTVKE
    ITGFLLIQAW PENRTDLHAF

421 ENLEIIRGRT KQHGQFSLAV VSLNITSLGL RSLKEISDGD
    VIISGNKNLC YANTINWKKL

481 FGTSGQKTKI ISNRGENSCK ATGQVCHALC SPEGCWGPEP
    RDCVSCRNVS RGRECVDKCN

541 LLEGEPREFV ENSECIQCHP ECLPQAMNIT CTGRGPDNCI
    QCAHYIDGPH CVKTCPAGVM

601 GENNTLVWKY ADAGHVCHLC HPNCTYGCTG PGLEGCPTNG
    PKIPSIATGM VGALLLLLVV

661 ALGIGLFMRR RHIVRKRTLR RLLQERELVE PLTPSGEAPN
    QALLRILKET EFKKIKVLGS

721 GAFGTVYKGL WIPEGEKVKI PVAIKELREA TSPKANKEIL
    DEAYVMASVD NPHVCRLLGI

781 CLTSTVQLIT QLMPFGCLLD YVREHKDNIG SQYLLNWCVQ
    IAKGMNYLED RRLVHRDLAA

841 RNVLVKTPQH VKITDFGLAK LLGAEEKEYH AEGGKVPIKW
    MALESILHRI YTHQSDVWSY

901 GVTVWELMTF GSKPYDGIPA SEISSILEKG ERLPQPPICT
    IDVYMIMVKC WMIDADSRPK

961 FRELIIEFSK MARDPQRYLV IQGDERMHLP SPTDSNFYRA
    LMDEEDMDDV VDADEYLIPQ

1021 QGFFSSPSTS RTPLLSSLSA TSNNSTVACI DRNGLQSCPI
     KEDSFLQRYS SDPTGALTED

1081 SIDDTFLPVP EYINQSVPKR PAGSVQNPVY HNQPLNPAPS
     RDPHYQDPHS TAVGNPEYLN

1141 TVQPTCVNST FDSPAHWAQK GSHQISLDNP DYQQDFFPKE
     AKPNGIFKGS TAENAEYLRV

1201 APQSSEFIGA
```

Again, the bolded and underlined sequences will be fused in the mLEEK peptide.

The present mLEEK sequence, retaining original amino acid numbering is as follows:

```
   1 M R P S G T A G A A L L A L L A A L C P A S R A L E E K K V  (SEQ ID NO: 5)

901 G V T V W E L M T F G S K P Y D G I P A S E I S S I L E K G

931 E R L P Q P P I C T I D V Y M I M V K C W M I D A D S R P K

961 F R E L I I E F S K M A R D P Q R Y L V I Q G D E R M H L P

991 S P T D S N F Y R A L M D E E D M D D V V D A D E Y L I P Q

1021 Q G F F S S P S T S R T P L L S S L S A T S N N S T V A C I

1051 D R N G L Q S C P I K E D S F L Q R Y S S D P T G A L T E D

1081 S I D D T F L P V P E Y I N Q S V P K R P A G S V Q N P V Y

1111 H N Q P L N P A P S R D P H Y Q D P H S T A V G N P E Y L N

1141 T V Q P T C V N S T F D S P A H W A Q K G S H Q I S L D N P

1171 D Y Q Q D F F P K E A K P N G I F K G S T A E N A E Y L R V

1201 A P Q S S F F I G A
```

The underlined tyrosine residues indicate potential phosphorylation sites. The sequence of FIG. 1A is bolded.

The mutant 1:24 sequence, retaining original amino acid numbering is as follows:

```
   1 M R P S G T A G A A L L A L L A A L C P A S R A L E E K K G  (SEQ ID NO: 7)
 951 W M I D A D S R P K F R E L I I E F S K M A R D P Q R Y L V
 981 I Q G D E R M H L P S P T D S N F Y R A L M D E E D M D D V
1011 V D A D E Y L I P Q Q G F F S S P S T S R T P L L S S L S A
1041 T S N N S T V A C I D R N G L Q S C P I K E D S F L Q R Y S
1071 S D P T G A L T E D S I D D T F L P V P] E Y I N Q S V P K R
1101 P A G S V Q N P V Y H N Q P L N P A P S R D P H Y Q D P H S
1131 T A V G N P E Y L N T V Q P T C V N S T F D S P A H W A Q K
1161 G S H Q I S L D N P D Y Q Q D F F P K E A K P N G I F K G S
1191 T A E N A E Y L R V A P Q S S E F I G A
```

The sequence of FIG. 1B is bolded.
The mutant 1:28 sequence, retaining original numbering, is as follows:

```
   1 M R P S G T A G A A L L A L L A A L C P A S R A L E E K K E (SEQ ID NO: 9)
1092 Y I N Q S V P K R P A G S V Q N P V Y H N Q P L N P A P S R
1122 D P H Y Q D P H S T A V G N P E Y L N I V Q P T C V N S T F
1152 D S P A H W A Q K G S H Q I S L D N P D Y Q Q D F F P K E A
1182 K P N G I F K G S T A E N A E Y L R V A P Q S S E F I G A
```

The sequence of FIG. 1C is bolded

The nucleotide sequence for the mLEEK propeptide is shown below, retaining the original nucleotide numbering sequence from X00588, where the ˆ indicates the junction between nucleotides 274 and 2888 (1:23 fusion). The first 207 nucleotides (underlined) would be omitted in the case of a nucleotide encoding the mature mLEEK polypeptide. The nucleotide sequence corresponding to the partial nucleotide sequence given in FIG. 1A (SEQ ID NO: 16) is bolded:

```
   1
     GCCGCGCTGCGCCGGAGTCCCGAGCTAGCCCCGGCGCCGCCGCCGCCCAGACCGGACGACAGGCC  (SEQ ID NO: 4)
     ACCTCGTCGGCGTCCGCCCGAGTCCCCGCCTCGCCGCCAACGCCACAACCACCGCGCACGGCCCC
     CTGACTCCGTCCAGTATTGATCGGGAGAGCCGGAGCGAGCTCTTCGGGGAGCAGCGATGCGACCC
     TCCGGGACGGCCGGGGGAGCAGCGATGCGACCCTCCGGGACGGCCGGGGCAGCGCTCCTGGCGCT
     GCTGGCTGCGCTCTGCCCGGCGAGTCGGGCTCTGGAGGAAAAGAAAGˆGGGTGACCGTTTGGGAG
     TTGATGACCTTTGGATCCAAGCCATATGACGGAATCCCTGCCAGCGAGATCTCCTCCATCCTGGA
     GAAAGGAGAACGCCTCCCTCAGCCACCCATATGTACCATCGATGTCTACATGATCATGGTCAAGT
     GCTGGATGATAGACGCAGATAGTCGCCCAAAGTTCCGTGAGTTGATCATCGAATTCTCCAAAATG
     GCCCGAGACCCCCAGCGCTACCTTGTCATTCAGGGGGATGAAAGAATGCATTTGCCAAGTCCTAC
     AGACTCCAACTTCTACCGTGCCCTGATGGATGAAGAAGACATGGACGACGTGGTGGATGCCGACG
     AGTACCTCATCCCACAGCAGGGCTTCTTCAGCAGCCCCTCCACGTCACGGACTCCCCTCCTGAGC
     TCTCTGAGTGCAACCAGCAACAATTCCACCGTGGCTTGCATTGATAGAAATGGGCTGCAAAGCTG
     TCCCATCAAGGAAGACAGCTTCTTGCAGCGATACAGCTCAGACCCCACAGGCGCCTTGACTGAGG
     ACAGCATAGACGACACCTTCCTCCCAGTGCCTGAATACATAAACCAGTCCGTTCCCAAAAGGCCC
     GCTGGCTCTGTGCAGAATCCTGTCTATCACAATCAGCCTCTGAACCCCGCGCCCAGCAGAGACCC
     ACACTACCAGGACCCCCACAGCACTGCAGTGGGCAACCCCGAGTATCTCAACACTGTCCAGCCCA
     CCTGTGTCAACAGCACATTCGACAGCCCTGCCCACTGGGCCCAGAAAGGCAGCCACCAAATTAGC
```

-continued

```
CTGGACAACCCTGACTACCAGCAGGACTTCTTTCCCAAGGAAGCCAAGCCAAATGGCATCTTTAA

GGGCTCCACAGCTGAAAATGCAGAATACCTAAGGGTCGCGCCACAAAGCAGTGAATTTATTGGAG

CATGACCACGGAGGATAGTATGAGCCCTAAAAATCCAGACTCTTTCGATACCCAGGACCAAG

3876
```

The nucleotide sequence for the present 1:24 mutant propeptide is shown below, retaining the original nucleotide numbering sequence from X00588, where the | indicates the junction between nucleotides 274 and 3035. The first 207 nucleotides (underlined) would be omitted in the case of a nucleotide encoding the mature 1:24 mutant polypeptide. The nucleotide sequence corresponding to the partial nucleotide sequence given in FIG. 1B (SEQ ID NO: 17) is bolded:

```
1
GCCGCGCTGCGCCGGAGTCCCGAGCTAGCCCCGGCGCCGCCGCCGCCCAGACCGGACGACAGGC   (SEQ ID NO: 6)

CACCTCGTCGGCGTCCGCCCGAGTCCCCGCCTCGCCGCCAACGCCACAACCACCGCGCACGGCC

CCCTGACTCCGTCCAGTATTGATCGGGAGAGCCGGAGCGAGCTCTTCGGGGAGCAGCGATGCGA

CCCTCCGGGACGGCCGGGGCAGCGCTCCTGGCGCTGCTGGCTGCGCTCTGCCCGGCGAGTCGGG

CTCTGGAGGAAAAGAAAG|GCTGGATGATAGACGCAGATAGTCGCCCAAAGTTCCGTGAGTTGA

TCATCGAATTCTCCAAAATGGCCCGAGACCCCCAGCGCTACCTTGTCATTCAGGGGATGAAAG

AATGCATTTGCCAAGTCCTACAGACTCCAACTTCTACCGTGCCCTGATGGATGAAGAAGACATG

GACGACGTGGTGGATGCCGACGAGTACCTCATCCCACAGCAGGGCTTCTTCAGCAGCCCCTCCA

CGTCACGGACTCCCCTCCTGAGCTCTCTGAGTGCAACCAGCAACAATTCCACCGTGGCTTGCAT

TGATAGAAATGGGCTGCAAAGCTGTCCCATCAAGGAAGACAGCTTCTTGCAGCGATACAGCTCA

GACCCCACAGGCGCCTTGACTGAGGACAGCATAGACGACACCTTCCTCCCAGTGCCTGAATACA

TAAACCAGTCCGTTCCCAAAAGGCCCGCTGGCTCTGTGCAGAATCCTGTCTATCACAATCAGCC

TCTGAACCCCGCGCCCAGCAGAGACCCACACTACCAGGACCCCCACAGCACTGCAGTGGGCAAC

CCCGAGTATCTCAACACTGTCCAGCCCACCTGTGTCAACAGCACATTCGACAGCCCTGCCCACT

GGGCCCAGAAAGGCAGCCACCCAAATTAGCCTGGACAACCCTGACTACCAGCAGGACTTCTTTCC

CAAGGAAGCCAAGCCAAATGGCATCTTTAAGGGCTCCACAGCTGAAAATGCAGAATACCTAAGG

GTCGCGCCACAAAGCAGTGAATTTATTGGAGCATGACCACGGAGGATAGTATGAGCCCTAAAAA

TCCAGACTCTTTCGATACCCAGGACCAAG

3876
```

The nucleotide sequence for the present 1:28 mutant propeptide is shown below, retaining the original nucleotide numbering sequence from X00588, where the / indicates the junction between nucleotides 274 and 3458. The first 207 nucleotides (underlined) would be omitted in the case of a nucleotide encoding the mature 1:28 mutant polypeptide. The nucleotide sequence corresponding to the partial nucleotide sequence given in FIG. 1C (SEQ ID NO: 18) is bolded:

```
1
GCCGCGCTGCGCCGGAGTCCCGAGCTAGCCCCGGCGCCGCCGCCGCCCAGACCGGACGACAGGC   (SEQ ID NO: 8)

CACCTCGTCGGCGTCCGCCCGAGTCCCCGCCTCGCCGCCAACGCCACAACCACCGCGCACGGCC

CCCTGACTCCGTCCAGTATTGATCGGGAGAGCCGGAGCGAGCTCTTCGGGGAGCAGCGATGCGA
```

-continued

```
CCCTCCGGGACGGCCGGGGCAGCGCTCCTGGCGCTGCTGGCTGCGCTCTGCCCGGCGAGTCGGG

CTCTGGAGGAAAAGAAAG/AATACATAAACCAGTCCGTTCCCAAAAGGCCCGCTGGCTCTGTGC

AGAATCCTGTCTATCACAATCAGCCTCTGAACCCCGCGCCCAGCAGAGACCCACACTACCAGGA

CCCCCACAGCACTGCAGTGGGCAACCCCGAGTATCTCAACACTGTCCAGCCCACCTGTGTCAAC

AGCACATTCGACAGCCCTGCCCACTGGGCCCAGAAAGGCAGCCACCAAATTAGCCTGGACAACC

CTGACTACCAGCAGGACTTCTTTCCCAAGGAAGCCAAGCCAAATGGCATCTTTAAGGGCTCCAC

AGCTGAAAATGCAGAATACCTAAGGGTCGCGCCACAAAGCAGTGAATTTATTGGAGCATGACCA

CGGAGGATAGTATGAGCCCTAAAAATCCAGACTCTTTCGATACCCAGGACCAAG

3876
```

Thus, the present mutant sequences contemplate SNPs and mutations reported as occurring approximately between amino acids numbered as 1-29 and 901-1210 (i.e., nucleotides 208-274 and 2888-3876 allowing for variations in numbering in different variants).

Thus, for example, the following exemplary SNPs are included within the specific sequences given here:

| dbSNP allele | Protein residue | Codon position | Amino acid position |
|---|---|---|---|
| C | Thr (T) | 3 | 903 |
| T | Thr [T] | 3 | 903 |
| G | Gly [G] | 1 | 962 |
| C | Arg [R] | 1 | 962 |
| T | Cys [C] | 1 | 977 |
| C | Arg [R] | 1 | 977 |
| C | Pro [P] | 2 | 988 |
| A | His [H] | 2 | 988 |
| T | Asp [D] | 3 | 994 |
| C | Asp [D] | 3 | 994 |

Furthermore, it is known that the EGFR is part of a family of tyrosine kinase receptors. The epidermal growth factor (EGF) family of receptor tyrosine kinases consists of four receptors, EGF-R (ErbB1), ErbB2 (Neu), ErbB3, and ErbB4. Members of the EGF-R family contain a cytoplasmic tyrosine kinase domain, a single transmembrane domain, and an extracellular domain that is involved in ligand binding and receptor dimerization. Activation of the EGF-R results in the initiation of a diverse array of cellular pathways. In response to toxic environmental stimuli, such as ultraviolet irradiation, or to receptor occupation by EGF, the EGF-R forms homo- or heterodimers with other family members. Thus, the present mLEEK sequences may encompass variants that may be conventionally be referred to as related to other EGFR family members.

Therefore, the sequences disclosed and claimed herein include variations in the mutant EGFR polypeptides and nucleic acid sequences given above. Guidance for such variations may be found by reference to sequences that are known to have similarities to the mLEEK amino acid sequence given above, particularly in the autophosphorylation domain. A BLAST search of this sequence in the NCBI nr database shows that mLEEK is considered to have significant homology to a number of proteins in the tyrosine kinase catalytic domain, which is the NCBI label given to the autophosphorylation region (mLEEK amino acids 901-1210, as numbered according to the original EGFR sequence).

Limiting the database to human sequences produced the following highest identities:

1. 49176515|gb|AAT52212.1| cell growth inhibiting protein 40 [Homo sapiens] (This sequence also contains the LEEKK motif)
2. 29725609|ref|NP_005219.2| epidermal growth factor receptor isoform a [Homo sapiens]
3. |757924|emb|CAA25240.1| epidermal growth factor receptor [Homo sapiens]
4. 223980|prf||1006266A epidermal growth factor receptor
5. 62088464|dbj|BAD92679.1| epidermal growth factor receptor isoform a variant [Homo sapiens]
6. 41473840|gb|AAS07524.1| unknown [Homo sapiens]
7. 63101670|gb|AAH94761.1| EGFR protein [Homo sapiens]

All of the above had 100% identity, except for the N terminal region of the 1:23 fusion. The following other known genes are examples of those which may be considered substantially identical for purposes of sequence variation in the region of the full length peptide outside of the splice variation, particularly the C terminal region:

1. gi|110825958|ref|NP_001036064.1| v-erb-a erythroblastic leukemia viral oncogene homolog 4 isoform;
2. gi|4885215|ref|NP_005226.1| v-erb-a erythroblastic leukemia viral oncogene homolog 4 isoform; JM-a/CVT-1 precursor [Homo sapiens];
3. gi|3913590|sp|Q15303|ERBB4_HUMAN Receptor tyrosine-protein kinase erbB-4 precursor (p180erbB4) (Tyrosine kinase-type cell surface receptor HER4);
4. gi|337360|gb|AAB59446.1| receptor tyrosine kinase;
5. gi|62088974|dbj|BAD92934.1| v-erb-a erythroblastic leukemia viral oncogene homolog 4 variant [Homo sapiens];
6. gi|306840|gb|AAA75493.1| HER2 receptor;
7. gi|27658000|gb|AAO18082.1| v-erb-b2 erythroblastic leukemia viral oncogene homolog 2, neuro/glioblastoma;
8. gi|54792096|ref|NP_004439.2| erbB-2 isoform a [Homo sapiens];
9. gi|119533|sp|P04626|ERBB2_HUMAN Receptor tyrosine-protein kinase erbB-2 precursor (p185erbB2) (C-erbB-2) (NEU proto-oncogene) (Tyrosine kinase-type cell surface receptor HER2) (MLN 19) (CD340 antigen);
10. gi|306841|gb|AAA35979.1| HER3 protein precursor;

For the sake of brevity, the full amino acid sequences, which are available by running a BLAST search at http://www.ncbi.nlm.nih.gov/BLAST/Blast.cgi, are not given here.

Identity at the N terminal region (but not the region C terminal to the splice) exists in epidermal growth factor receptor isoform b and isoform d [Homo sapiens].

The above sequences provide guidance for varying the specific sequences given herein to a certain degree while retaining the utilities described here. Thus, the mutant EGFR sequences subject to the present invention are termed "substantially identical," as the term is defined here. It is preferred that the amino acid sequence be found to be identical using the BLAST scoring set forth above, and that the sequence retain kinase signaling function. At the DNA level, the same percentages would hold true, although more variation can be expected due to the degeneracy of the genetic code.

Using RT-PCR for primers that spanned from the AUG start site of protein translation to the stop codon, there is described below the identification of certain truncated transcripts, including the transcript corresponding to mLEEK. Total RNA was isolated from U87-MG cells and reverse transcribed and amplified using the Qiagen One-Step RTPCR kit (Catalog#210212) with primers listed below.

```
FORWARD PRIMER EGFR 176-196
5'GGGGAGCAGCGATGCGACCCT 3'         (SEQ ID NO: 19)

REVERSE PRIMER EGFR 3877-3857
5'GCTTGGTCCTGGGTATCGAAA 3'         (SEQ ID NO: 20)
```

The 1088 bp product was sequenced comprehensively and the in frame exon 1-23 junction was identified.

Using RT-PCR, this transcript was found in 8 of 8 breast (100%), 8 of 13 (62%) ovarian, and 5 of 7 (71%) colon tumors. The transcript was also found in gastric tumors.

To confirm the presence of mLEEK, RNase protection assays using a probe that spans the unique junction were also performed. This confirmed that this junction was indeed present in A431 cells. (The A431 cell line was derived from an 85-year-old female with epidermal carcinoma). The cells carry large numbers of EGF binding sites and are indicator cells for EGF or TGF-α binding. The probe is an antisense RNA probe spanning the exon 1-23 junction. This includes 72 nucleotides of exon 1 and 96 nucleotides of exon 23. The probe was made by transcription with T7 RNA polymerase. There are an additional 28 nucleotides of nonhomology included at the 3' end of the probe to permit discrimination of the full size probe from the protected RNA fragment. The sequence used is as follows with the T7 promoter sequences being underlined:

```
                                            (SEQ ID NO: 21)
5'TAATACGACTCACTATAGGGAGGAGGCGTTCTCCTTTCTCCAGGGATG

GAGGAGATCTCGCTGGCAGGATTCCGTCATATGGCTTGGATCCAAAGGTC

ATCAACTCCCAAACGGTCACCCCTTTCTTTTCCTCCAGAGCCCGACTCGC

CGGGCAGAGCGCAGCCAGCAGCGCCAGGAGCGCTGCCCCGGCCGTGCCCC

GGGTTCTATAGTGTCACCTAAAT 3'
```

Example 9 describes the preparation, using a peptide corresponding to the unique junction present in mLEEK, of an antibody that specifically recognized mLEEK and not normal EGF receptor or EGFRvIII. A peptide corresponding to the mLEEK junction with an additional cysteine at the C-terminus for the purpose of conjugation was synthesized. The sequence of the peptide was LEEKKGVTVWELC. (SEQ ID NO: 22) This peptide was then conjugated to maleimide activated keyhole limpet hemocyanin (KLH) at a 1:1 (wt/wt) ratio and then used to immunize rabbits. (KLH is one of a number of suitable foreign carrier proteins used to enhance hapten immunogenicity. See, The Journal of Immunology, 2000, 164: 4797-4803.)

The resulting antisera was tested and confirmed to only recognize mLEEK, and not EGF receptor or EGFRvIII. Western blots using this antibody confirmed the presence of the protein in several cell lines including U87-MG, A431, 293T, HEK293, MDA-MB-468, and HeLa. Analysis of several tumors by Western blot using this antibody showed that mLEEK is present in 5 of 6 brain tumors and 6 of 8 colon tumors. When compared to normal tissue, mLEEK was expressed at higher amounts than in normal brain or colon.

To study its physiologic functions, a cell line was derived that overexpresses mLEEK (See Example 4). In soft agar colony formation assays, it was found that this cell line had increased anchorage independent growth as compared to the parental control cell line. This data indicates that the overexpression of mLEEK can confer tumorigenic properties onto cells.

Using the antibody against mLEEK, immunofluorescence microscopy was performed to determine where the protein was localized. This revealed that a significant proportion of the protein was present in the nucleus (See FIG. 5). Cell fractionation studies confirmed that 50% of the mLEEK protein was found in the nucleus. This nuclear localization raised the possibility that mLEEK might affect transcription of certain genes. To examine this, cells were transfected with a plasmid encoding mLEEK and a luciferase reporter construct containing the promoter for c-fos. (See Example 12). This revealed that the presence of mLEEK significantly augmented transcription from the c-fos promoter. Thus, mLEEK can induce the transcription of certain genes. To see if this was via a complex that directly interacted with the promoter, the antibody against mLEEK was used in chromatin immunoprecipitation experiments. This demonstrated that this antibody could precipitate a DNA fragment containing a portion of the c-fos promoter. From this it was concluded that mLEEK is present in a complex that directly associates with this promoter. Similar results were also found for the b-myb promoter.

Because mLEEK contains a signal peptide, but lacks a transmembrane region, it is possible that mLEEK is secreted from the cell. As shown in FIG. 13 and Example 5B, the culture media from NIH-3T3 cells expressing HA tagged mLEEK or U87-MG cells, which are known to express mLEEK, was studied over a 24 h time period. Using antibodies against mLEEK, it was found that mLEEK accumulated in the media, indicating that it was secreted from cells.

The identification of mLEEK demonstrates that a naturally occurring portion of the EGF receptor can localize efficiently to the nucleus where it is capable of activating the transcription of genes involved in cell growth. Functional assays show that cells overexpressing mLEEK show the tumorigenic properties of cancer cells. The mLEEK protein is overexpressed in several human cancers as compared to normal tissues. Thus, mLEEK can promote the growth of cancer cells. Because the protein is secreted, it can act on adjacent or distant cells to affect gene transcription and hence phenotypes such as cell growth.

Natural sequence polymorphisms are also included within the present mLEEK, some of which might be of functional significance. Site directed mutagenesis may be employed to create mLEEK cDNA molecules that either inactivate or augment its biologic properties. Other variations include deletion or insertional mutants. The proteins produced by these mutant cDNAs can also be used for specific therapeutic purposes to either enhance or interfere with specific biologic processes.

DEFINITIONS

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "identical" or "identity" in the context of two nucleic acids or polypeptide sequences refers to the residues in the two sequences, which are the same when aligned for maximum correspondence. Optimal alignment of sequences for comparison can be conducted, e.g., by the local homology algorithm of Smith and Waterman, *Adv. Appl. Math.* 2: 482 (1981), by the homology alignment algorithm of Needleman and Wunsch, *J. Mol. Biol.* 48:443 (1970), by the search for similarity method of Pearson and Lipman, *Proc. Natl. Acad. Sci.* (U.S.A.) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

As applied to polypeptides, the term "substantial identity," or "substantially identical," means that two peptide sequences, when optimally aligned, such as by the programs BLAST, GAP or BESTFIT using default gap weights, share at least 40 percent sequence identity, preferably at least 90 percent sequence identity, more preferably at least 95, 96, 97, or 98 percent sequence identity, and most preferably at least 99 percent sequence identity over the entire length of the peptide being considered. Preferably, residue positions, which are not identical, differ by conservative amino acid substitutions. As discussed herein, minor variations in the amino acid sequences of the inventive polypeptides are contemplated as being encompassed by the present invention, providing that the variations in the amino acid sequence maintain at least 75%, more preferably at least 80%, 90%, 95%, and most preferably 99%. Conservative amino acid substitutions are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; phenylalanine, tryptophan, and tyrosine are an aromatic family, and cysteine and methionine a sulfur-containing side chain family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Preferred conservative amino acid substitution groups are: valine-leucine-isoleucine, phenylalanine-tyrosine, lysine-arginine, alanine-valine, glutamic acid-aspartic acid, cysteine-methionine, and asparagine-glutamine.

An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

Two polynucleotides are substantially identical according to the above description, i.e., the term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like, An indication that two nucleotide sequences are substantially identical is that the polypeptide, which the first nucleic acid encodes, is immunologically cross reactive with the polypeptide encoded by the second nucleic acid.

Another indication that two nucleotide sequences are substantially identical is that the two molecules hybridize to each other under stringent conditions. Stringent conditions are sequence dependent and are different under different environmental parameters. Generally, stringent conditions are selected to be about 5° C. to 20° C. lower than the thermal melting point (T[m]) for the specific sequence at a defined ionic strength and pH. The T[m] is the temperature (under defined ionic strength and pH) at which 50% of the target sequence hybridizes to a perfectly matched probe. However, nucleic acids, which do not hybridize to each other under stringent conditions, are still substantially identical if the polypeptides, which they encode, are substantially identical. This occurs, e.g., when a copy of a nucleic acid is created using the maximum codon degeneracy permitted by the genetic code.

The phrases "specifically binds" or "specifically hybridizes to" or "specifically immunoreactive with," refers to a binding reaction, which is determinative of the presence of the protein or polynucleotide in the presence of a heterogeneous population of proteins or polynucleotides and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, N.Y., for a description of immunoassay formats and conditions that can be used to determine specific immunoreactivity. An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope, in particular, binding to a mutant EGFR peptide without significant binding to wild type EGFR. Preferably, the antibody of the present invention specifically binds to mLEEK with dissociation constant Kd equal to or lower than 100 nM, optionally lower than 10 nM, optionally lower than 1 nM, optionally lower than 0.5 nM, optionally lower than 0.1 nM, optionally lower than 0.01 nM, or optionally lower than 0.005 nM, in the form of monoclonal antibody, scFv, Fab, or other form of antibody measured at a temperature of about 4° C., 25° C., 37° C. or 42° C.

Specific hybridization is carried out between complementary polynucleotides under stringent conditions. The term "specifically hybridizes" thus means that the probe hybridizes to the target sequence, and not to non-target sequences, e.g., to mutant EGFR polynucleotide but not wild type EGFR polynucleotide, at a level which allows ready identification of probe/target sequence hybridization under selective hybridization conditions.

The terms "isolated," "purified," or "biologically pure" refer to material that is substantially or essentially free from components which normally accompany it as found in its native state.

The term "antibody" as used herein, further includes various forms of modified or altered antibodies, such as an intact immunoglobulin, antibody fragments such as an Fv fragment, an Fv fragment containing only the light and heavy chain variable regions, an Fv fragment linked by a disulfide bond (Brinkmann, et al., *Proc. Natl. Acad. Sci. USA*, 90: 547-551 (1993)), a Fab or (Fab)'2 fragment containing the variable regions and parts of the constant regions, a single-chain antibody and the like (Bird et al., *Science* 242: 424-426 (1988); Huston et al., *Proc. Nat. Acad. Sci. USA* 85: 5879-5883 (1988)). The antibody may be of animal (especially mouse or rat) or human origin or may be chimeric (Morrison et al., *Proc Nat. Acad. Sci. USA* 81: 6851-6855 (1984)) and is preferably humanized (Jones et al., *Nature* 321: 522-525 (1986), and published UK patent application #8707252). The term "human antibody" therefore refers to antibodies containing sequences of human origin, except for possible non-human CDR regions, and does not imply that the full structure of an Ig molecule be present, only that the antibody has minimal immunogenic effect in a human.

The present "antibody fragments" include Fab, Fab', F(ab')2, and Fv fragments; diabodies; linear antibodies (Zapata et al., *Protein Eng.* 8(10): 1057-1062 (1995)); single-chain antibody molecules; and multi specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen binding sites and is still capable of cross-linking antigen.

"Fv" is the minimum antibody fragment that contains a complete antigen-recognition and -binding site. This region consists of a dimer of one heavy- and one light chain variable domain in tight, non-covalent association. It is in this configuration that the three CDRS of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The present antibodies include "diabodies," which refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993). The presently contemplated antibodies also include "minibodies," as described, e.g., at U.S. Pat. No. 5,837,821.

In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody, other protein, or nucleic acid is "isolated" if it has been identified and separated and/or recovered from a component of its natural environment. Contaminant components of its natural environment are materials that would interfere with diagnostic or therapeutic uses for the molecule, and may include enzymes, hormones, and other proteinaceous or nonproteinaceous solutes.

The terms "peptide," "polypeptide" and "protein" are used interchangeably herein to refer to an amino acid chain with two or more amino acid residues, and also includes branched and circularized amino acid chains.

The terminology "X#Y" in the context of a mutation in a polypeptide sequence is art-recognized, where "#" indicates the location of the mutation in terms of the amino acid number of the polypeptide, "X" indicates the amino acid found at that position in the wild-type amino acid sequence, and "Y" indicates the mutant amino acid at that position. For example, the notation "L688P" with reference to the EGFR polypeptide indicates that there is a leucine at amino acid number 688 of the wild-type EGFR sequence, and that leucine is replaced with a proline in the mutant EGFR sequence.

As used herein, the twenty conventional amino acids and their abbreviations follow conventional usage. See Immunology—A Synthesis (2<nd> Edition, E. S. Golub and D. R. Gren, Eds., Sinauer Associates, Sunderland, Mass. (1991)), which is incorporated herein by reference. The term "amino acid" or "amino acid residue," as used herein, refers to naturally occurring L amino acids (presently preferred) or to D amino acids. The commonly used one- and three-letter abbreviations for amino acids are used herein (Bruce Alberts et al., *Molecular Biology of the Cell*, Garland Publishing, Inc., New York (4th ed. 2002)). Stereoisomers (e.g., D-amino acids) of the twenty conventional amino acids, unnatural amino acids such as [alpha]-, [alpha]-disubstituted amino acids, N-alkyl amino acids, lactic acid, and other unconventional amino acids may also be suitable components for polypeptides of the present invention. Examples of unconventional amino acids include: 4-hydroxyproline, [gamma]-carboxyglutamate, [epsilon]-N,N,N-trimethyllysine, [epsilon]-N-acetyllysine, O-phosphoserine, N-acetylserine, N-formylmethionine, 3-methylhistidine, 5-hydroxylysine, [sigma]-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end; the lefthand direction of double-stranded polynucleotide sequences is referred to as the 5' direction. The direction of 5' to 3' in addition of nascent RNA transcripts is referred to as the transcription direction. Sequence regions on the DNA strand having the same sequence as the RNA and which are 5' to the 5' end of the RNA transcript are referred to as "upstream sequences," with downstream sequences being correspondingly 3'.

EXAMPLES

Example 1

Identification of Variant EGF Receptor Using PCR

It has recently been discovered that point mutations in the kinase domain of the EGF receptor predict clinical responsiveness to therapy with small molecule kinase inhibitors (Paez J G, Janne P A, Lee J C, Tracy S, Greulich H, Gabriel S et al., EGFR mutations in "Lung Cancer: Correlation with Clinical Response to Gefitinib Therapy," *Science* 2004; 304: 1497-1500. Lynch T J, Bell D W, Sordella R, Gurubhagavatula S, Okimoto R A, Brannigan B W et al., "Activating mutations in the epidermal growth factor receptor underlying responsiveness of non-small-cell lung cancer to gefitinib," *N Engl J Med* 2004; 350(21):2129-2139). We asked whether similar mutations might occur in the context of the EGFRvIII molecule that is frequently detected in glioblastoma. RT (reverse transcriptase)-PCR conditions were optimized using a forward primer within the first exon of the EGFR gene and a reverse primer immediately downstream of the tyrosine kinase domain. The sequence of those primers is:

```
176-196:    GGGGAGCAGCGATGCGACCCT (SEQ ID NO: 19)
3012-2992:  ATCGATGGTACATATGGGTGG (SEQ ID NO: 23)
```

This was followed by nested PCR using a set of primers that were non-overlapping. The sequence of those primers is:

```
202-222:    ACGGCCGGGGCAGCGCTCCTG (SEQ ID NO: 24)
2984-2964:  AGGCGTTCTCCTTTCTCCAGG (SEQ ID NO: 25)
```

These conditions were applied to RNA from primary tumor samples. The tumor samples were obtained from surgery and frozen until used to prepare RNA. The PCR products derived from several tumor samples [8 of 8 breast (100%); 8 of 13 (62%) ovarian; 5 of 7 (71%) colon] were significantly smaller than that expected for wild type EGF receptor or EGFRvIII and sequencing of the PCR products revealed this band represented the junction between exons 1 and 23 (data not shown).

This was confirmed by RT-PCR using the above sets of forward and reverse primers. In order to validate the presence of the unique sequence created by the junction of exons 1 and 23, ribonuclease protection assays were conducted. This involves the synthesis of a RNA sequence that is antisense to the sequence being interrogated. Following hybridization of this probe to total RNA, the reaction is treated with RNaseA+ T1, which will degrade regions of noncomplementarity so that the probe remains intact only if there are no regions of mismatch. Details of the probe are in the description of FIG. 3. A431 cells, an ovarian carcinoma cell line, were chosen for this analysis by RNase protection and revealed the strong presence of an intact exon 1 to 23 junction. This severely truncated splice variant represents a deletion that maintains the open reading frame of the message while generating a novel glycine codon at the fusion point. See FIG. 1A.

RT-PCR in breast, ovarian, and colon tumors, as well as several cell lines: HEK293, A431, HeLa and U87, detected a 2613-base pair in-frame EGFR deletion resulting in the joining of exons 1 to 23 and the generation of a novel glycine residue at the fusion point. Because it has the first four amino acids derived from exon 1, but is highly truncated relative to EGFRvIII, this variant receptor molecule was termed mini-LEEK (abbreviated mLEEK). A schematic view of its organization relative to other EGFRs is shown in FIG. 2. As shown there, the protein structure of mLEEK compared to wild type EGF receptor and EGFRvIII shows that mLEEK lacks the EGF ligand binding domain, transmembrane domain, and most of the tyrosine kinase domain, including the ATP binding site, yet retains all major autophosphorylation sites.

Example 2

RNase Protection Assay Confirming Unique Sequence

Figure 3:
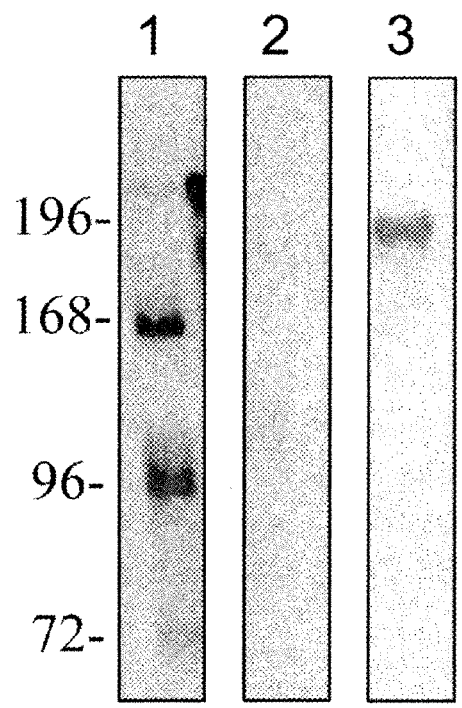
FIG. 3 is a photograph showing results of an RNase protection assay. A biotin-labeled antisense RNA probe was used for the RNase protection assays. Lane 1, A431 total RNA, Lane 2, yeast RNA, Lane 3, no-RNase control to show size of the full-length probe.

The nucleic acid structure of mLEEK was elucidated as shown in FIG. 3. As shown there, RNase protection showed an mLEEK RNA of the appropriate size. The probe is 196 nt. in length, where 72 nt. are from exon 1 and 96 nt. come from exon 23, with an additional 28 nt of noncomplementarity to permit discrimination between full length probe and protected fragments. Using this probe, the protected fragment corresponding to the junction of exons 1 and 23 would be 168 nt. Lane 1, A431, a squamous cell carcinoma cell line, total RNA, Lane 2, yeast RNA, Lane 3, no-RNase control to show size of the full-length probe.

RNase protection assays conducted with this probe discriminated between mLEEK and other isoforms of the receptor, as the unique exon structure of mLEEK is protected by the full length probe (FIG. 3). In order to quantitate wild type EGFR transcript levels, a probe may be synthesized within the exon 2-7 region that is deleted in both EGFRvIII and mLEEK. Preliminary experiments ensure that each probe is present in sufficient excess of its target mRNA to yield quantitative results. The relative level of each isoform in a given total RNA sample can then be determined by using all three probes in a single RNase protection assay.

Example 3

Stable Expression of mLEEK in U87MG Glioblastoma Cells

Figure 4:
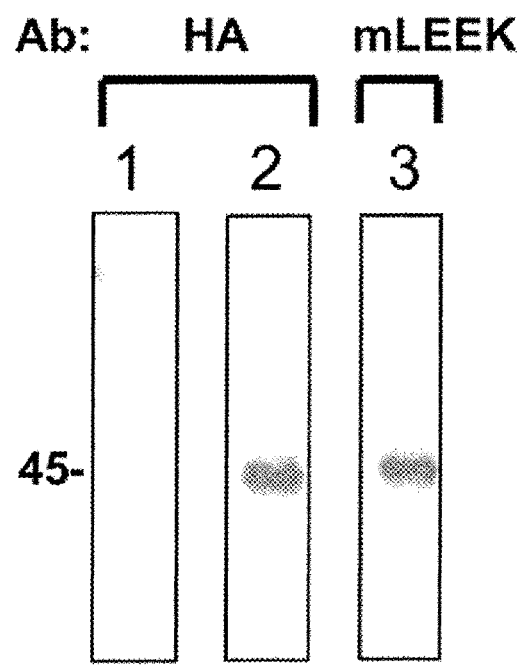
FIG. 4 is a photograph of a Western blot showing stable expression of mLEEK in U87MG (U87MG/mLEEK) glioblastoma cells. An HA-tagged mLEEK construct was transfected into U87MG cells and lysates were blotted with either antibodies against HA or mLEEK. Lane 1, parental U87MG lysate; Lanes 2 and 3, U87MG/mLEEK lysate.

We developed an HA epitope-tagged expression construct containing the cDNA that is generated by the exon 1 to 23 junction. This construct, which contained the entire protein-coding region of mLEEK and a tag for hemagglutinin (HA) at the COOH terminus, was transfected into U87MG human glioblastoma cell lines and stable transfectants were selected for by G-418 resistance. Using Western blots of cell lysates incubated with anti-HA monoclonal antibody (obtained from Covance), clones expressing high levels of HA tagged mLEEK were identified. Rabbits were also immunized with a synthetic 13mer peptide derived from the junction of exons 1 to 23: LEEKKGVTVWELC (SEQ ID NO: 22), where the underlined glycine is generated by the fusion of exons and the terminal cysteine was added for purposes of conjugation to KLH. Immunization was with the following formulation according to the following dosage and immunization schedule, every 20 days for 4 cycles followed by a bleeding 10 d. later. This sera was used for Western blots and compared to blots using anti-HA, and both antibodies identified an approximately 45 kDa protein, which is in accordance with the 37 kDa that is predicted based on the sequence, given the likely phosphorylation state of the molecule (FIG. 4).

Example 4

Stable Transfection of mLEEK into NIH 3T3 Cells

Figure 9:
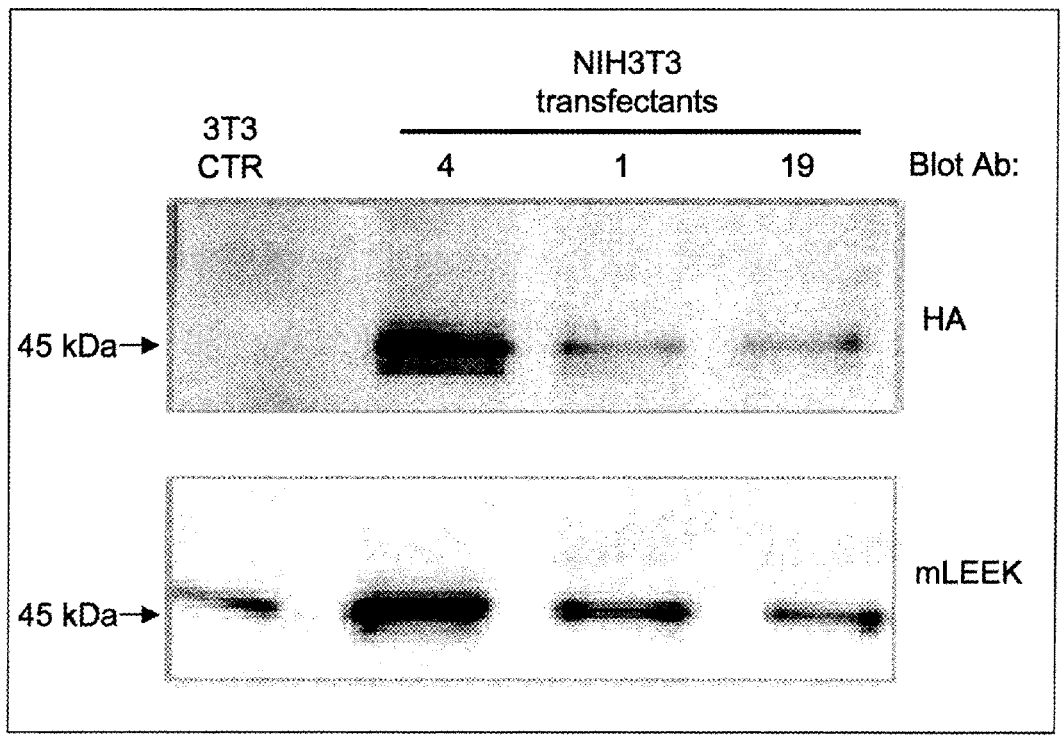
FIG. 9 is a photograph of two Western blots from an experiment where NIH3T3 fibroblast cells were transfected with either an HA-tagged mLEEK cDNA construct or empty vector control (3T3-CTR) and selected for G418-resistance.

Referring now to FIG. 9, fibroblast cells were transfected with either an HA-tagged mLEEK cDNA construct or empty vector control (3T3-CTR) and selected for G418-resistance.

Three individual colonies, indicated as 4, 1 and 19, representing NIH 3T3 transfected clones mLEEK-1, mLEEK-4 and mLEEK-19, were expanded and screened for mLEEK expression by blotting lysates with either antibodies against HA or mLEEK. Both antibodies detected an approximately 45 kDa protein that is identical in size to the protein seen in tumors, showing expression of mLEEK in these cells.

Example 5A

Analysis of the Distribution of mLEEK in U87MG Cells

Referring now to FIG. 5, in order to study the subcellular localization of mLEEK, U87MGmLEEK cells were examined by immunofluorescence with antibody to mLEEK. Secondary antibody conjugated to FITC was used for detection with confocal microscopy.

The photographs show that the preincubation with the immunizing peptide (FIG. 5C) showed an abolition of the nuclear staining while this was unaffected by the non-specific peptide (FIG. 5D). The results indicate that mLEEK is located in both the cytoplasm and the nucleus (FIGS. 5A and D), with a concentration in the nucleus.

Example 5B

Analysis of the Presence of mLEEK in the Media Surrounding the Cells

Figure 11:
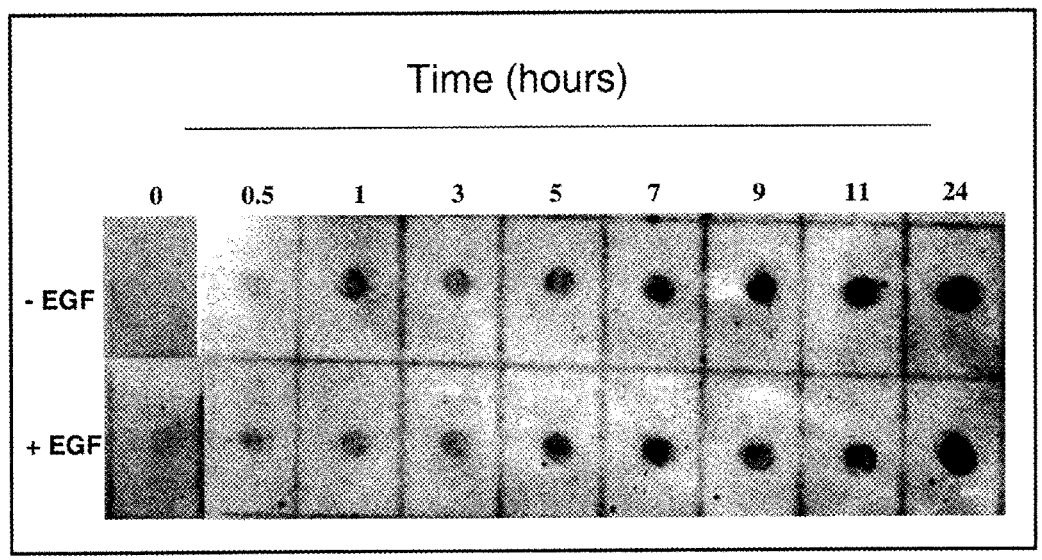
FIG. 11 is a photograph of a chemiluminescence assay, which shows the secretion of mLEEK into the media.

To determine if mLEEK is secreted from the cell, tissue culture media was collected from dishes containing U87-MG or 3T3-mLEEK-4 cells over a 24 h period, with or without EGF stimulation lower and upper panels, respectively, in FIG. 11). Media was dotted directly onto nitrocellulose and the filter incubated with anti-mLEEK antibody followed by secondary antibody. This revealed an accumulation of mLEEK in the media over time that was not significantly changed by the addition of EGF.

As shown in FIG. 11, presence of mLEEK in the conditioned media, assayed by blotting the nitrocellulose with anti-mLEEK antibody followed by HRP linked anti-rabbit secondary antibody and detection by chemiluminescence, showed an accumulation of mLEEK with time indicating that it is secreted from cells. Similar results were obtained for parental NIH3T3 cells as well as U87-MG cells.

Example 6 mLEEK is Tyrosine Phosphorylated

This example, referring to FIG. 6, shows that the mLEEK molecule retains all of the major autophosphorylation sites at its C-terminal end and thus is a likely target for phosphorylation by EGFR, EGFRvIII and possibly other tyrosine kinases. To determine the overall tyrosine phosphorylation status of mLEEK, NIH-3T3mLEEK cells may be serum starved and stimulated with EGF prior to lysis. mLEEK can be purified from cell lysates by immunoprecipitation with antibodies to the HA tag and used for Western blots with antibodies to phosphotyrosine. For further verification, a set of antibodies directed against each specific phosphotyrosine in the autophosphorylation domain of the EGF receptor can be used for detection of immunoprecipitations. It is anticipated that addition of EGF promotes phosphorylation of mLEEK. As described below, Western blot assays performed with antibodies directed against EGFRvIII have identified a ~45 kDa protein that is overexpressed relative to the 175 kDa wild type EGFR and the 145 kDa EGFRvIII in some tumors. The similarity in amino acid coding sequence shared by EGFRvIII and mLEEK may explain this cross-reactivity.

Results from red and green staining with anti-EGFRvIII and anti-pY, respectively, show that mLEEK is tyrosine phosphorylated (data not shown). Tumor cell lysate (TB99) and cells expressing EGFRvIII (HC2) were simultaneously incubated with anti-EGFRvIII directly conjugated to Alexa-Fluor 680 and anti-phosphotyrosine directly conjugated to IRDye 800. Images were separately acquired and then merged to reveal bands that are double labeled. There was a single band detected by anti-EGFRvIII (arrow) in TB99 which was also recognized by anti-phosphotyrosine as demonstrated by the merged image. The images showed a number of indistinct bands in the HC2 and TB99 cells, with the band in question present in the TB99 cells. EGF receptor autophosphorylation site specific antibodies detected the same 45 kDa protein.

FIG. 6(A) shows Western blots from a series of ovarian tumors designated 95, 00, 99 and 93. The full name given in these experiments would be TB95, etc. and they correspond to primary ovarian tumor biopsy samples. These cells were incubated with an antibody specific for EGFRvIII or anti-phosphotyrosine. While none of the 4 tumors was positive for EGFRvIII, a 45 kDa band was detected (indicated by arrow). A parallel blot with Anti-PY (FIG. 6A right) showed that the 45 kDa band was recognized by anti-phosphotyrosine antibodies. In FIG. 6B, Tumor 99 was incubated with a series of EGF receptor autophosphorylation site-specific antibodies. This revealed that the 45 kDa band (indicated by arrow) was recognized by antibodies against Y1173 and Y1148, and to a lesser extent by antibodies against Y1068 and Y845. (IgG indicates non-specific cross reaction by the secondary antibody with IgG heavy chain). The location of these phosphorylated tyrosines may be further seen with reference to SEQ ID NO: 5, giving the mLEEK amino acid sequence.

Example 7

Expression of mLEEK in Primary Tumors

Figure 7:
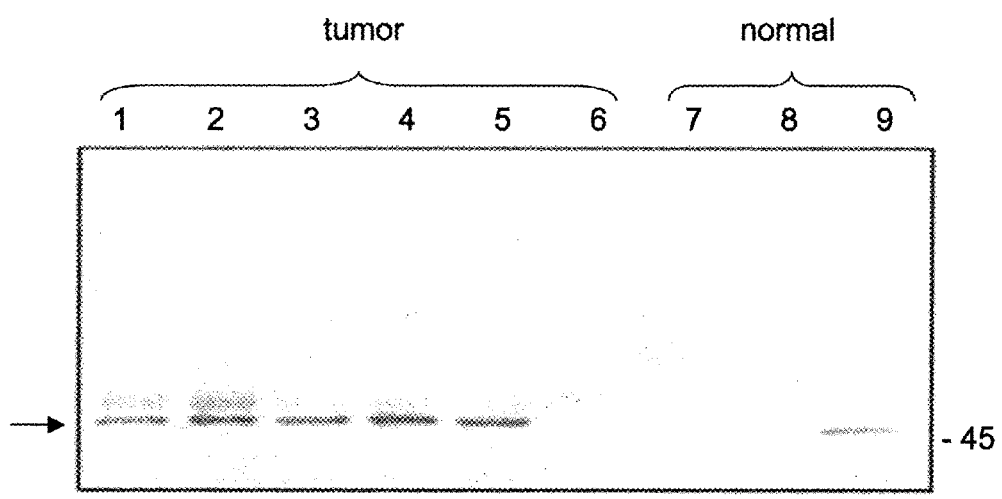
FIG. 7 is a photograph of a Western blot showing expression of mLEEK in primary glioblastoma tumors. Western blots containing lysates from human specimens were incubated with anti-mLEEK antibody followed by HRP linked anti-rabbit secondary antibody with detection by chemiluminescence. Lanes 1-6 show six unique glioblastoma specimens; Lanes 7-9 show normal tissue from 3 different human brains. Arrow indicates the mLEEK band; the band above is recognized by secondary antibody.

Referring now to FIG. 7, the expression of mLEEK in primary tumors was detected by Western blotting using a customized mLEEK specific polyclonal antibody raised against the exon 1 to 23 junction. Western blots using anti-mLEEK sera were performed on a series of glial tumors (lanes 1-6) and normal brain specimens (lanes 7-9). mLEEK is shown as a 45 kD band (indicated by arrow). The faint band above mLEEK is background recognized by secondary antibody. This showed that mLEEK was highly overexpressed in 5 of 6 tumors examined, but was detected in lysates from only 1 of 3 normal brain specimens.

The following table shows a summary of mLEEK expression detected in a panel of tumors by RT-PCR followed with nested PCR and sequence analysis. This also indicates the expression of mLEEK in breast, ovarian and colon tumors.

TABLE 1

Expression of mLEEK in human tumors detected by RT-PCR

| Tumor | MLEEK expression in % |
| --- | --- |
| Breast | 100 (8/8) |
| Ovarian | 62 (8/13) |
| Colon | 71 (5/7) |

Example 8

Expression of mLEEK in Fibroblasts Increases Anchorage Independent Growth

Figure 8:
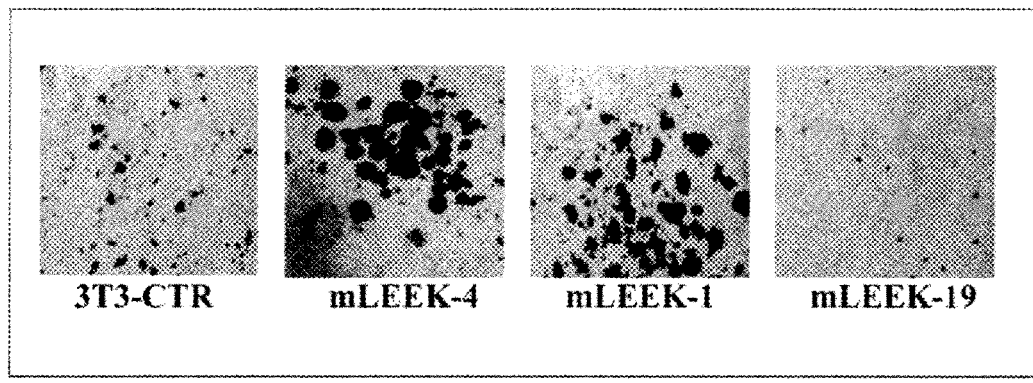
FIG. 8 is a series of four photographs showing soft agar colony formation by NIH3T3 transfectant clones (which were termed 3T3-mLEEK-1, 3T3-mLEEK-4 and 3T3-mLEEK-19) stably expressing varying levels of mLEEK (relative order 3T3-mLEEK-4>3T3-mLEEK-1>3T3-mLEEK-19) or empty expression vector (3T3-CTR). This shows that mLEEK expression promotes anchorage-independent growth.

Referring now to FIG. 8, we assessed soft agar colony formation by NIH3T3 transfectant clones stably expressing varying levels of mLEEK (the relative order of mLEEK protein expression in these clones is 3T3-mLEEK-4>3T3-mLEEK-1>3T3-mLEEK-19) or empty expression vector (3T3-CTR). It can be seen from the figure that soft agar colony formation is greater in the higher expressing clones. Anchorage-independent growth is one of the hallmarks of transformation, which is considered the most accurate and stringent in vitro assay for detecting malignant transformation of cells. The soft agar colony formation assay is a common method to monitor anchorage-independent growth, which measures proliferation in a semisolid culture media.

Example 9

Antibodies to mLEEK

A polyclonal antibody has been raised in rabbits immunized with a synthetic 13mer peptide derived from the junction of exons 1 to 23, and we have demonstrated that the unpurified antibody recognizes mLEEK in cell lines and tumors. To perform immunoprecipitations and other experiments where purified antibody is highly desirable, the sera may be affinity purified using this peptide conjugated to Sepharose. This antibody may be used for immunoblotting a broad spectrum of lysates from primary tissue and tumors, or mLEEK from serum or culture media. Paraffin embedded sections can be de-paraffinized in graded xylenes followed by antigen retrieval using citrate buffers while frozen sections will be used directly for staining. Slides are blocked with 1% serum, and then incubated with antibody at the appropriate dilution, washed, incubated with a biotinylated secondary antibody, washed again, and then incubated with the avidin-biotin-horseradish peroxidase complex. Following additional washes, the slide is incubated with the diaminobenzidine substrate with $H_2O_2$ as the catalyst. To ensure quality control, all staining runs should include a mLEEK transfected cell line as a positive control and pre-immune antibody as the negative control.

Example 10 siRNA to Downregulate Levels of mLEEK

The therapeutic potential of RNA interference in connection with EGFR has been shown in experiments with siRNA targeted to the unique junction of exons 1 and 8 (Fan Q W, Weiss W A. "RNA interference against a glioma-derived allele of EGFR induces blockade at G2M," Oncogene 2005; 24(5):829-837).

The junction of exons 1 and 23 in mLEEK creates a unique region that may be targeted for specific silencing by RNA interference. Within this region, there are several potential siRNA target sequences revealed by design algorithms.

These sequences are:

5'- AAAAGAAAGGGGTGACCGTTT -3'    (SEQ ID NO: 26)

5'- AAGAAAGGGGTGACCGTTTGG -3'    (SEQ ID NO: 27)

5'- AAAGGGGTGACCGTTTGGGAG -3'    (SEQ ID NO: 28)

Expression of mLEEK may be silenced by transfecting synthetic siRNAs using Lipofectamine 2000 (Invitrogen) into the stably transfected cell line. Mismatch siRNAs will be included as non-specific controls. One may assay for effective knockdown (greater than 70 percent) of mRNA levels using RT-PCR. Effective siRNA have been developed for EGFRvIII, and one would expect that this can be done as described here with mLEEK. Once identified, one may use this siRNA as the basis for the generation of shRNA vectors and then establish cell lines that stably express this shRNA.

Example 11

Quantitative Evaluation of mLEEK Transcription

For quantitative comparisons of the relative level of each transcript in the cell, real-time RT-PCR may be employed, as it is extremely sensitive and offers high reproducibility. The full-length wild type EGFR mRNA may be exclusively amplified from total RNA using primers located within the regions corresponding to exons 2 through 7, as these exons are deleted from both EGFRvIII and mLEEK. EGFRvIII and mLEEK may each be selectively amplified by designing primers to overlap the unique junction specific to each variant. Optimization of RT-PCR conditions to eliminate non-specific background and validation of primer specificity by sequencing of cDNA products will permit the use of SYBR green fluorogenic dye for detection and quantification of product. An alternative is to employ a more specific method of detection that is dependent upon fluorescence resonance energy transfer (FRET) for the generation of fluorescence signal such as the commercially available Taqman probes.

Example 12 mLEEK is in a Complex that Binds DNA

Figure 10:
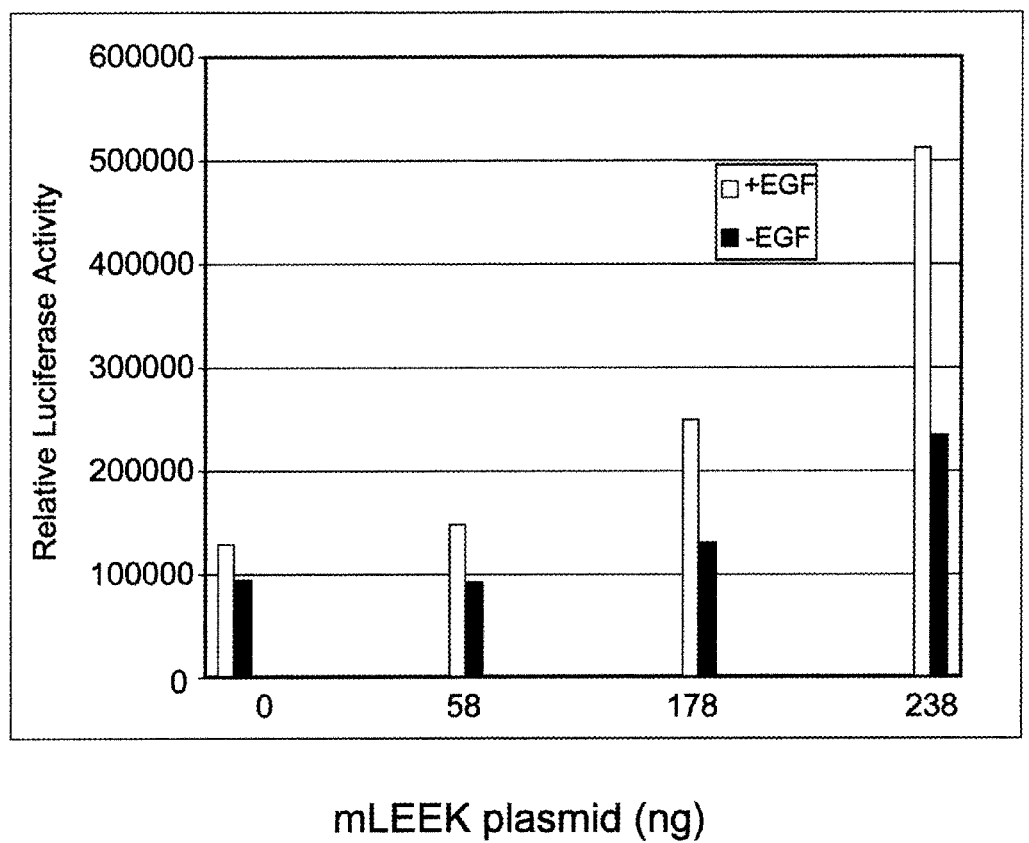
FIG. 10 is a graph showing activation of the c-Fos promoter in a dose-dependent manner by expression of mLEEK.

To show activation of c-fos-mediated transcription, a Luc reporter plasmid was constructed by cloning nucleotides −356 to +109 from the c-fos promoter upstream of the luciferase reporter gene. HEK293 cells were cotransfected with 238 ng of this reporter and either 0, 58, 178, or 238 ng of expression vector containing the mLEEK cDNA. After serum starvation for 24 hours, cells were stimulated with 100 ng/mL EGF for 9 hours, harvested, and subjected to luciferase assay. The results are shown in FIG. 10, and show a dose-dependent increase in transcribed luciferase resulting from addition of mLEEK (EGF addition indicated as "EGF"). Mean data were calculated from two independent experiments.

Chromatin immunoprecipitation (ChIP) experiments were performed on NIH-3T3 cells serum starved for 24 hours and stimulated with 100 ng/mL EGF for 30 min. This assay is based on the fact that DNA-bound proteins (including transcription factors) in living cells can be cross-linked to the chromatin on which they are situated.

Each ChIP experiment used $2\times10^6$ cells. Protein complexes bound to DNA were cross-linked using formaldehyde, sonicated, and then immunoprecipitated with 3 uL of polyclonal anti-mLEEK sera overnight. The cross links were then reversed and the DNA used as a template for PCR. MDA-MB468 cells for human promoters, or NIH-3T3 cells for mouse promoters, were serum starved and then treated with 100 ng/ml EGF for 30 min. The cells were then used in ChIP experiments with either the antibody against mLEEK or pre-immune serum as the negative control. Detection of associated promoters was performed by using PCR to detect the DNA fragment that was precipitated by binding to mLEEK.

This work showed that the human c-fos and b-Myb promoters specifically associated with mLEEK, as well as the mouse c-fos promoter.

The mouse cFOS PCR primers used were:

```
eFOS 173-196:
GCTGCACCCTCAGAGTTGGCTGCA      (SEQ ID NO: 29)

eFOS 697-674:
AAGTTTGGGGAAAGCCCGGCAAGG      (SEQ ID NO: 30)
```

Example 13

Other Splice Variants Shorter than mLEEK

Exon 1 to 24

In addition to the exon 1 to 23 fusion described above (See FIG. 1), the present inventors have also found an exon 1 to 24 junction EGFR mutant. This mutant is characterized by a deletion of exons 2 through 23. The junction is between nucleotides 274 (as in mLEEK) and nucleotide 3035. At the amino acid level, this is a joining of amino acids 25 to 951 (using the numbering of the intact protein) or 1 to 927 (using the numbering of the mature protein).

The sequence of immediate junction is <u>LEEKK GWMIDADSR</u> (SEQ ID NO: 31). The junction is shown with underlining in the full sequence illustrated below. The above glycine is created by the junction and is novel.

Exon 1 to 28

This mutant has a deletion of exons 2 to 27, resulting in the joining of nucleotides 274 to 3458, using the numbering system above. This results in the joining of amino acids 25 to 1091 (as numbered in the intact protein) or 1 to 1067 (as numbered in the mature protein).

The sequence in the vicinity of the junction is LEEKK^EY-INQSVP (where ^ indicates point of junction) (SEQ ID NO: 11). The downstream sequence is illustrated by dotted underline below.

The amino acid position of these deletions are shown in SEQ ID NO:14 below, where * indicates the point of junction in mLEEK, the sequence in ( ) is deleted in the exon 1 to 24 junction mutant, and the sequence in (] is deleted in the 1 to 28 junction mutant (using amino acid sequence of X00588).

```
  1 M R P S G T A G A A L L A L L A A L C P A S R A L E E K K (V    SEQ ID NO: 14

31 C Q G T S N K L T Q L G T F E D H F L S L Q R M F N N C E V

61 V L G N L F I T Y V Q R N Y D L S F L K T I Q E V A G Y V L

91 I A L N T V E R I P L E N L Q I I R G N M Y Y E N S Y A L A

121 V L S N Y D A N K T G L K E L P M R N L Q E I L H G A V R F

151 S N N P A L C N V E S I Q W R D I V S S D F L S N M S M D F

181 Q N H L G S C Q K C D P S C P N G S C W G A G E E N C Q K L

211 T K I I C A Q Q C S G R C R G K S P S D C C H N Q C A A G C

241 T G P R E S D C L V C R K F R D E A T C K D T C P P L M L Y

271 N P T T Y Q M D V N P E G K Y S F G A T C V K K C P R N Y V

301 V T D H G S C V R A C G A D S Y E M E E D G V R K C K K C E

331 G P C R K V C N G I G I G E F K D S L S I N A T N I K H F K

361 N C T S I S G D L H I L P V A F R G D S F T H T P P L D P Q
```

-continued

```
391  E L D I L K T V K E I T G F L L I Q A W P E N R T D L H A F
421  E N L E I I R G R T K Q H G Q F S L A V V S L N I T S L G L
451  R S L K E I S D G D V I I S G N K N L C Y A N T I N W K K L
481  F G T S G Q K T K I I S N R G E N S C K A T G Q V C H A L C
511  S P E G C W G P E P R D C V S C R N V S R G R E C V D K C K
541  L L E G E P R E F V E N S E C I Q C H P E C L P Q A M N I T
571  C T G R G P D N C I Q C A H Y I D G P H C V K T C P A G V M
601  G E N N T L V W K Y A D A G H V C H L C H P N C T Y G C T G
631  P G L E G C P T N G P K I P S I A T G M V G A L L L L L V V
661  A L G I G L F M R R R H I V R K R T L R R L L Q E R E L V E
691  P L T P S G E A P N Q A L L R I L K E T E F K K I K V L G S
721  G A F G T V Y K G L W I P E G E K V K I P V A I K E L R E A
751  T S P K A N K E I L D E A Y V M A S V D N P H V C R L L G I
781  C L T S T V Q L I T Q L M P F G C L L D Y V R E H K D N I G
811  S Q Y L L N W C V Q I A K G M N Y L E D R R L V H R D L A A
841  R N V L V K T P Q H V K I T D F G L A K L L G A E E K E Y H
871  A E G G K V P I K W M A L E S I L H R I Y T H Q S D V W S Y
901  *G V T V W E L M T F G S K P Y D G I P A S E I S S I L E K G
931  E R L P Q P P I C T I D V Y M I M V K C) W M I D A D S R P K
961  F R E L I I E F S K M A R D P Q R Y L V I Q G D E R M H L P
991  S P T D S N F Y R A L M D E E D M D D V V D A D E Y L I P Q
1021 Q G F F S S P S T S R T P L L S S L S A T S N N S T V A C I
1051 D R N G L Q S C P I K E D S F L Q R Y S S D P T G A L T E D
1081 S I D D T F L P V P] E Y I N Q S V P  K R P A G S V Q N P V
     Y
1111 H N Q P L N P A P S R D P H Y Q D P H S T A V G N P E Y L N
1141 T V Q P T C V N S T F D S P A H W A Q K G S H Q I S L D N P
1171 D Y Q Q D F F P K E A K P N G I F K G S T A E N A E Y L R V
1201 A P Q S S E F I G A
```

The nucleotide position of the deletions described above is given below in SEQ ID NO: 32, where the nucleotide sequence in ( ) is deleted in the exon 1 to 24 junction mutant, and the nucleotide sequence in (] is deleted in the 1 to 28 junction mutant (using nucleotide sequence of X00588).

```
  1 GCCGCGCTGC GCCGGAGTCC CGAGCTAGCC CCGGCGCCGC CGCCGCCCAG ACCGGACGAC    SEQ ID NO: 32

61 AGGCCACCTC GTCGGCGTCC GCCCGAGTCC CCGCCTCGCC GCCAACGCCA CAACCACCGC

121 GCACGGCCCC CTGACTCCGT CCAGTATTGA TCGGGAGAGC CGGAGCGAGC TCTTCGGGGA

181 GCAGCGATGC GACCCTCCGG GACGGCCGGG GCAGCGCTCC TGGCGCTGCT GGCTGCGCTC

241 TGCCCGGCGA GTCGGGCTCT GGAGGAAAAG AAAG(TTTGCC AAGGCACGAG TAACAAGCTC

301 ACGCAGTTGG GCACTTTTGA AGATCATTTT CTCAGCCTCC AGAGGATGTT CAATAACTGT

361 GAGGTGGTCC TTGGGAATTT GGAAATTACC TATGTGCAGA GGAATTATGA TCTTTCCTTC
```

-continued

```
 421 TTAAAGACCA TCCAGGAGGT GGCTGGTTAT GTCCTCATTG CCCTCAACAC AGTGGAGCGA
 481 ATTCCTTTGG AAAACCTGCA GATCATCAGA GGAAATATGT ACTACGAAAA TTCCTATGCC
 541 TTAGCAGTCT TATCTAACTA TGATGCAAAT AAAACCGGAC TGAAGGAGCT GCCCATGAGA
 601 AATTTACAGG AAATCCTGCA TGGCGCCGTG CGGTTCAGCA ACAACCCTGC CCTGTGCAAC
 661 GTGGAGAGCA TCCAGTGGCG GGACATAGTC AGCAGTGACT TTCTCAGCAA CATGTCGATG
 721 GACTTCCAGA ACCACCTGGG CAGCTGCCAA AAGTGTGATC CAAGCTGTCC CAATGGGAGC
 781 TGCTGGGGTG CAGGAGAGGA GAACTGCCAG AAACTGACCA AAATCATCTG TGCCCAGCAG
 841 TGCTCCGGGC GCTGCCGTGG CAAGTCCCCC AGTGACTGCT GCCACAACCA GTGTGCTGCA
 901 GGCTGCACAG GCCCCCGGGA GAGCGACTGC CTGGTCTGCC GCAAATTCCG AGACGAAGCC
 961 ACGTGCAAGG ACACCTGCCC CCCACTCATG CTCTACAACC CCACCACGTA CCAGATGGAT
1021 GTGAACCCCG AGGGCAAATA CAGCTTTGGT GCCACCTGCG TGAAGAAGTG TCCCCGTAAT
1081 TATGTGGTGA CAGATCACGG CTCGTGCGTC CGAGCCTGTG GGGCCGACAG CTATGAGATG
1141 GAGGAAGACG GCGTCCGCAA GTGTAAGAAG TGCGAAGGGC CTTGCCGCAA AGTGTGTAAC
1201 GGAATAGGTA TTGGTGAATT TAAAGACTCA CTCTCCATAA ATGCTACGAA TATTAAACAC
1261 TTCAAAAACT GCACCTCCAT CAGTGGCGAT CTCCACATCC TGCCGGTGGC ATTTAGGGGT
1321 GACTCCTTCA CACATACTCC TCCTCTGGAT CCACAGGAAC TGGATATTCT GAAAACCGTA
1381 AAGGAAATCA CAGGGTTTTT GCTGATTCAG GCTTGGCCTG AAAACAGGAC GGACCTCCAT
1441 GCCTTTGAGA ACCTAGAAAT CATACGCGGC AGGACCAAGC AACATGGTCA GTTTTCTCTT
1501 GCAGTCGTCA GCCTGAACAT AACATCCTTG GGATTACGCT CCCTCAAGGA GATAAGTGAT
1561 GGAGATGTGA TAATTTCAGG AAACAAAAAT TTGTGCTATG CAAATACAAT AAACTGGAAA
1621 AAACTGTTTG GGACCTCCGG TCAGAAAACC AAAATTATAA GCAACAGAGG TGAAAACAGC
1681 TGCAAGGCCA CAGGCCAGGT CTGCCATGCC TTGTGCTCCC CCGAGGGCTG CTGGGGCCCG
1741 GAGCCCAGGG ACTGCGTCTC TTGCCGGAAT GTCAGCCGAG GCAGGGAATG CGTGGACAAG
1801 TGCAAGCTTC TGGAGGGTGA GCCAAGGGAG TTTGTGGAGA ACTCTGAGTG CATACAGTGC
1861 CACCCAGAGT GCCTGCCTCA GGCCATGAAC ATCACCTGCA CAGGACGGGG ACCAGACAAC
1921 TGTATCCAGT GTGCCCACTA CATTGACGGC CCCCACTGCG TCAAGACCTG CCCGGCAGGA
1981 GTCATGGGAG AAAACAACAC CCTGGTCTGG AAGTACGCAG ACGCCGGCCA TGTGTGCCAC
2041 CTGTGCCATC CAAACTGCAC CTACGGATGC ACTGGGCCAG GTCTTGAAGG CTGTCCAACG
2101 AATGGGCCTA AGATCCCGTC CATCGCCACT GGGATGGTGG GGGCCCTCCT CTTGCTGCTG
2161 GTGGTGGCCC TGGGGATCGG CCTCTTCATG CGAAGGCGCC ACATCGTTCG GAAGCGCACG
2221 CTGCGGAGGC TGCTGCAGGA GAGGGAGCTT GTGGAGCCTC TTACACCCAG TGGAGAAGCT
2281 CCCAACCAAG CTCTCTTGAG GATCTTGAAG GAAACTGAAT TCAAAAAGAT CAAAGTGCTG
2341 GGCTCCGGTG CGTTCGGCAC GGTGTATAAG GGACTCTGGA TCCCAGAAGG TGAGAAAGTT
2401 AAAATTCCCG TCGCTATCAA GGAATTAAGA GAAGCAACAT CTCCGAAAGC AACAAGGAA
2461 ATCCTCGATG AAGCCTACGT GATGGCCAGC GTGGACAACC CCCACGTGTG CCGCCTGCTG
2521 GGCATCTGCC TCACCTCCAC CGTGCAACTC ATCACGCAGC TCATGCCCTT CGGCTGCCTC
2581 CTGGACTATG TCCGGGAACA CAAAGACAAT ATTGGCTCCC AGTACCTGCT CAACTGGTGT
2641 GTGCAGATCG CAAAGGGCAT GAACTACTTG GAGGACCGTC GCTTGGTGCA CCGCGACCTG
2701 GCAGCCAGGA ACGTACTGGT GAAAACACCG CAGCATGTCA AGATCACAGA TTTTGGGCTG
2761 GCCAAACTGC TGGGTGCGGA AGAGAAAGAA TACCATGCAG AAGGAGGCAA AGTGCCTATC
2821 AAGTGGATGG CATTGGAATC AATTTTACAC AGAATCTATA CCCACCAGAG TGATGTCTGG
```

```
2881 AGCTACGGGG TGACCGTTTG GGAGTTGATG ACCTTTGGAT CCAAGCCATA TGACGGAATC

2941 CCTGCCAGCG AGATCTCCTC CATCCTGGAG AAAGGAGAAC GCCTCCCTCA GCCACCCATA

3001 TGTACCATCG ATGTCTACAT GATCATGGTC AAGT)GCTGGA TGATAGACGC AGATAGTCGC

3061 CCAAAGTTCC GTGAGTTGAT CATCGAATTC TCCAAAATGG CCCGAGACCC CCAGCGCTAC

3121 CTTGTCATTC AGGGGATGA AAGAATGCAT TTGCCAAGTC CTACAGACTC CAACTTCTAC

3181 CGTGCCCTGA TGGATGAAGA AGACATGGAC GACGTGGTGG ATGCCGACGA GTACCTCATC

3241 CCACAGCAGG GCTTCTTCAG CAGCCCCTCC ACGTCACGGA CTCCCCTCCT GAGCTCTCTG

3301 AGTGCAACCA GCAACAATTC CACCGTGGCT TGCATTGATA GAAATGGGCT GCAAAGCTGT

3361 CCCATCAAGG AAGACAGCTT CTTGCAGCGA TACAGCTCAG ACCCCACAGG CGCCTTGACT

3421 GAGGACAGCA TAGACGACAC CTTCCTCCCA GTGCCTG]AAT ACATAAACCA GTCCGTTCCC

3481 AAAAGGCCCG CTGGCTCTGT GCAGAATCCT GTCTATCACA ATCAGCCTCT GAACCCCGCG

3541 CCCAGCAGAG ACCCACACTA CCAGGACCCC CACAGCACTG CAGTGGGCAA CCCCGAGTAT

3601 CTCAACACTG TCCAGCCCAC CTGTGTCAAC AGCACATTCG ACAGCCCTGC CCACTGGGCC

3661 CAGAAAGGCA GCCACCAAAT TAGCCTGGAC AACCCTGACT ACCAGCAGGA CTTCTTTCCC

3721 AAGGAAGCCA AGCCAAATGG CATCTTTAAG GGCTCCACAG CTGAAAATGC AGAATACCTA

3781 AGGGTCGCGC CACAAAGCAG TGAATTTATT GGAGCATGAC CACGGAGGAT AGTATGAGCC

3841 CTAAAAATCC AGACTCTTTC GATACCCAGG ACCAAGCCAC AGCAGGTCCT CCATCCCAAC

3901 AGCCATGCCC GCATTAGCTC TTAGACCCAC AGACTGGTTT TGCAACGTTT ACACCGACTA

3961 GCCAGGAAGT ACTTCCACCT CGGGCACATT TTGGGAAGTT GCATTCCTTT GTCTTCAAAC

4021 TGTGAAGCAT TTACAGAAAC GCATCCAGCA AGAATATTGT CCCTTTGAGC AGAAATTTAT

4081 CTTTCAAAGA GGTATATTTG AAAAAAAAAA AAAAGTATA TGTGAGGATT TTTATTGATT

4141 GGGGATCTTG GAGTTTTTCA TTGTCGCTAT TGATTTTTAC TTCAATGGGC TCTTCCAACA

4201 AGGAAGAAGC TTGCTGGTAG CACTTGCTAC CCTGAGTTCA TCCAGGCCCA ACTGTGAGCA

4261 AGGAGCACAA GCCACAAGTC TTCCAGAGGA TGCTTGATTC CAGTGGTTCT GCTTCAAGGC

4321 TTCCACTGCA AACACTAAA GATCCAAGAA GGCCTTCATG GCCCCAGCAG GCCGGATCGG

4381 TACTGTATCA AGTCATGGCA GGTACAGTAG GATAAGCCAC TCTGTCCCTT CCTGGGCAAA

4441 GAAGAAACGG AGGGGATGAA TTCTTCCTTA GACTTACTTT TGTAAAAATG TCCCCACGGT

4501 ACTTACTCCC CACTGATGGA CCAGTGGTTT CCAGTCATGA GCGTTAGACT GACTTGTTTG

4561 TCTTCCATTC CATTGTTTTG AAACTCAGTA TGCCGCCCCT GTCTTGCTGT CATGAAATCA

4621 GCAAGAGAGG ATGACACATC AAATAATAAC TCGGATTCCA GCCCACATTG GATTCATCAG

4681 CATTTGGACC AATAGCCCAC AGCTGAGAAT GTGGAATACC TAAGGATAAC ACCGCTTTTG

4741 TTCTCGCAAA AACGTATCTC CTAATTTGAG GCTCAGATGA AATGCATCAG GTCCTTTGGG

4801 GCATAGATCA GAAGACTACA AAAATGAAGC TGCTCTGAAA TCTCCTTTAG CCATCACCCC

4861 AACCCCCCAA AATTAGTTTG TGTTACTTAT GGAAGATAGT TTTCTCCTTT TACTTCACTT

4921 CAAAAGCTTT TTACTCAAAG AGTATATGTT CCCTCCAGGT CAGCTGCCCC CAAACCCCCT

4981 CCTTACGCTT TGTCACACAA AAAGTGTCTC TGCCTTGAGT CATCTATTCA AGCACTTACA

5041 GCTCTGGCCA ACAGGGCA TTTTACAGGT GCGAATGACA GTAGCATTAT GAGTAGTGTG

5101 AATTCAGGTA GTAAATATGA AACTAGGGTT TGAAATTGAT AATGCTTTCA CAACATTTGC

5161 AGATGTTTTA GAAGGAAAAA AGTTCCTTCC TAAAATAATT TCTCTACAAT TGGAAGATTG

5221 GAAGATTCAG CTAGTTAGGA GCCCATTTTT TCCTAATCTG TGTGTGCCCT GTAACCTGAC
```

```
5281 TGGTTAACAG CAGTCCTTTG TAAACAGTGT TTTAAACTCT CCTAGTCAAT ATCCACCCCA

5341 TCCAATTTAT CAAGGAAGAA ATGGTTCAGA AAATATTTTC AGCCTACAGT TATGTTCAGT

5401 CACACACACA TACAAAATGT TCCTTTTGCT TTTAAAGTAA TTTTTGACTC CCAGATCAGT

5461 CAGAGCCCCT ACAGCATTGT TAAGAAAGTA TTTGATTTTT GTCTCAATGA AAATAAAACT

5521 ATATTCATTT CC
```

Example 14

Peptide Formulations

The present peptides may be formulated for purposes of inducing an immune response to the corresponding mutant EGFR. Vaccine formulations are well known in the art, as exemplified in U.S. Pat. No. 6,090,388 to Wang, issued Jul. 18, 2000, entitled "Peptide composition for prevention and treatment of HIV infection and immune disorders." This patent teaches the use of a sequence homologous to a portion of the CDR-2 like domain of CD4, covalently linked to a helper T cell epitope, and optionally to other immunostimulatory sequences as well. Using the present teachings, one may adapt such formulations to use with the present EGFR mutant peptides to provide the use of such peptides as immunogens to elicit the production in a host of high titer polyclonal auto-antibodies, and also cytotoxic T cells, which are specific to the corresponding mutant EGFR expressed in the host. Thus, Class II Th epitopes termed promiscuous Th evoke efficient T cell help and can be combined with synthetic B cell epitopes that by themselves are poorly immunogenic to generate potent peptide immunogens (U.S. Pat. No. 5,759,551). One may further induce the desired CD8+ T cell response by the use of CpG. See, *J Clin Invest.* 2005 Mar. 1; 115(3): 739-746. Accordingly, the peptide composition of the invention can be formulated as an immunogenic composition using adjuvants, emulsifiers, pharmaceutically-acceptable carriers or other ingredients routinely provided in vaccine compositions. Adjuvants or emulsifiers that can be used in this invention include alum, incomplete Freund's adjuvant, liposyn, saponin, squalene, L121, emulsigen, monophosphoryl lipid A (MPL), QS21, ISA206, and ISA 720, as well as other known efficacious adjuvants and emulsifiers. Such formulations are readily determined by one of ordinary skill in the art and also include formulations for immediate release and/or for sustained release, and for induction of systemic immunity and/or induction of localized mucosal immunity, which may be accomplished, for example, by immunogen entrapment or by coadministration with microparticles. As another embodiment of the present peptide formulations, one may prepare the peptides specifically for topical use. See, U.S. Pat. No. 6,797,276 to Glenn, et al., issued Sep. 28, 2004, entitled "Use of penetration enhancers and barrier disruption agents to enhance the transcutaneous immune response."

The peptides here taught can also be prepared for pharmaceutical use by incorporating them with a pharmaceutically acceptable carrier or diluent. Thus, a further aspect of the present invention provides pharmaceutical compositions comprising a peptide from an exon 1:23, 1:24 or 1:28 mutant of EGFR as described herein and a pharmaceutically acceptable carrier or diluent. The peptide can be prepared for pharmaceutical use by incorporating it in unit dosage form as tablets or capsules for oral or parenteral administration either alone or in combination with suitable carriers such as calcium carbonate, starch, lactose, talc, magnesium stearate, and gum acacia. The peptide can be formulated for oral, parenteral or topical administration in aqueous solutions, aqueous alcohol, glycol or oil solutions or oil-water emulsions. Buffered-aqueous or carrier mediated aqueous/non-aqueous intrathecal and intravenous dosages can be formulated. These and other suitable forms for the pharmaceutical compositions of the invention can be found, for example, in Remington's Pharmaceutical Science, 15th ed., Mack Publishing Company, Easton, Pa. (1980). The pharmaceutical compositions of the invention can comprise any combination of one or both of the peptides. Further guidance in the preparation and administration of the present EGFR mutant vaccines may be found in Heimberger et al., "Epidermal Growth Factor Receptor VIII Peptide Vaccination Is Efficacious against Established Intracerebral Tumors," Clinical Cancer Research Vol. 9, 4247-4254, Sep. 15, 2003. This study, done in mice, showed that vaccination with an EGFRvIII-specific peptide is efficacious against both s.c. and established intracerebral tumors. PEP-3, a 13-amino acid peptide with a terminal cysteine (LEEKKGNYVVT-DHC, SEQ ID NO: 3) that spans the EGFRvIII mutation, was synthesized at AnaSpec, Inc. (San Jose, Calif.). The purity of the peptide preparation was >95%, as assessed by high-pressure liquid chromatography. The peptide was conjugated to KLH at a 1:1 ratio (w/w) and used for immunization. The immunogens were diluted in distilled H2O to a concentration of 2 mg/ml.

Example 15

Relationship of mLEEK to the Endoplasmic Reticulum Stress Response

Because we hypothesized that mLEEK was involved in the transcriptional regulation of proteins, we elected to perform an analysis of gene expression in cells that were transfected with mLEEK. 100 mm$^2$ dishes of HT1080 fibrosarcoma cells were transfected with 4.4 or 8.8 μg of either mLEEK expression plasmid or control plasmid in duplicate and the RNA was harvested 48 hours later. The RNA was then labeled with dCTP nucleotides containing either Cy3 or Cy5 fluorochrome, and this labeled probe was hybridized with the Human Exonic Evidence Based Oligonucleotide (HEEBO) array fabricated by the Stanford Genomics facility, which contains over 44,544 oligonucleotides. Using the signal from the array that was hybridized with RNA extracted from cells transfected with control plasmid to normalize the signals, the fold change in signal intensity was calculated for each oligonucleotide and was reported to the log(base2). The EGF receptor gene was consistently detected as one of the highest fold induced genes (4-8 fold induction) in all mLEEK transfected plates, but this was ascribed to the fact that the transcript was derived from the transfected gene; indeed, oligonucleotides corresponding to exons absent in mLEEK were not increased in expression. Beta-actin also showed a significant increase in all mLEEK transfected plates as did two genes containing ankyrin repeat domains, ARD30B and ARD27. The significance of the increase in these genes is unclear since an insufficient amount is known about ARD30B and ARD27 and the increase in beta-actin may be non-specific. However, examination of genes that showed ~2 fold or greater increase consistently revealed several proteins that are involved in the endoplasmic reticulum (ER) stress response, including Homocysteine-induced endoplasmic reticulum protein (HERP), an ER-resident membrane protein which has a ubiquitin (Ub)-like domain at its N-terminus; 78 kDa glucose regulated protein (Grp78/BiP), a molecular chaperone that has been implicated in protein folding and calcium sequestration in the ER, and whose transcription is enhanced by ER stress; 94 kDa glucose regulated protein (Grp94), an ER chaperone glycoprotein; a chaperonin; and a gene similar to peptidylprolyl isomerase A. A table from a representative experiment is shown below:

TABLE 2

Genes showing ~2 fold induction in response to mLEEK transfection (8.8 ug in 100 mm² dishes). EGF receptor and beta-actin related proteins have been removed for clarity.

| NAME | Gene Name | Log(base2) of R/G Normalized Ratio (Mean) |
|---|---|---|
| hSQ001735 | Ankyrin repeat domain 30B | 3.361 |
| hSQ044883 | UDP-GlcNAc:betaGal beta-1,3-N-acetylglucosaminyltransferase 3 | 2.271 |
| hSQ004704 | Transgene | 1.815 |
| hSQ000887 | Transgene | 1.784 |
| hSQ004704 | Transgene | 1.676 |
| hSQ000887 | Transgene | 1.627 |
| hSQ016210 | Solute carrier family 2, (facilitated glucose transporter) member 8 | 1.613 |
| hSQ024963 | Transgene | 1.606 |
| hSQ034623 | Nanos homolog 3 (*Drosophila*) | 1.487 |
| hSQ003140 | Homocysteine-inducible, endoplasmic reticulum stress-inducible, ubiquitin-like domain member 1 (HERP) | 1.425 |
| hSQ024963 | Transgene | 1.416 |
| hSQ027363 | Ankyrin repeat domain 27 (VPS9 domain)::regulator of G protein signaling 9-binding protein | 1.364 |
| hSQ030217 | Heat shock 70 kDa protein 5 (glucose-regulated protein, 78 kDa)(Grp 78/BiP) | 1.319 |
| hSQ004206 | | 1.318 |
| hSQ027620 | Transgene_small_t_Ag_specific Small t specific_166 | 1.277 |
| hSQ019263 | RNA, U3 small nucleolar | 1.26 |
| hSQ000887 | Transgene | 1.244 |
| hSQ043533 | Heat shock protein 90 kDa beta (Grp94), member 1 | 1.241 |
| hSQ020613 | Cysteine-rich with EGF-like domains 2 | 1.159 |
| hSQ024418 | Hypothetical protein LOC144871 | 1.127 |
| hSQ001222 | Heat shock protein 90 kDa beta (Grp94), member 1 | 1.096 |
| hSQ032233 | Protein disulfide isomerase family A, member 4 | 1.071 |
| hSQ027620 | Transgene_small_t_Ag_specific Small t specific_166 | 1.064 |
| hSQ042222 | Stromal cell-derived factor 2-like 1 | 1.049 |
| hSQ033393 | **Chaperonin containing TCP1, subunit 6A (zeta 1)-like | 1.042 |
| hSQ026522 | Tribbles homolog 3 (*Drosophila*) | 1.027 |
| hSQ033392 | UCSC_hg16 | 1.024 |
| hSQ027620 | Transgene_small_t_Ag_specific Small t specific_166 | 1.01 |
| hSQ024963 | Transgene | 1.001 |
| hSQ044405 | similar to peptidylprolyl isomerase A isoform 1 | 0.989 |

The ER stress response is a cellular mechanism that has been highly conserved from yeast to humans to deal with an increase in the expression of proteins. As more proteins are being translated, the ER senses the increase in demand on protein folding and using a highly conserved program that relies on the novel splicing of the X-box-binding protein (XBP-1) transcription factor. In addition, it can increase the expression of certain chaperones, such as Grp94 and Grp78/BiP, to handle the increased load. Should the cell fail to keep up with the increased demands, the cell will undergo apoptosis. An increase in the ER stress response is seen in many pathologic states including ischemia due to stroke or heart attack, diabetes, cancer, cystic fibrosis, bipolar disorder, and neurodegenerative disorders such as Alzheimer's disease and Parkinson's disease, and Huntington's disease. (See Hiderou et al., "ER Stress and Diseases", FEBS Journal, Volume 274, Number 3, February 2007, pp. 630-658(29)).

mLEEK may have a role in directly activating the transcription of these genes, but it was possible that the overexpression of mLEEK itself induced the ER stress response. To distinguish between these two possibilities, we obtained a cell line that contains an XBP cDNA construct that is fused out of frame with the luciferase gene. If the XBP transcript undergoes splicing induced by ER stress, the luciferase gene is placed in-frame with XBP and becomes active. Cells were transfected with mLEEK, and as negative controls we used an expression vector for the HA tag alone or a construct expressing yellow fluorescent protein (YFP). As a positive control for induction of ER stress, cells were treated with the drug thapsigargin (Tg), which is widely used to induce ER stress via blocking the Ca+2 ATPase of the ER leading to increased cytoplasmic Ca+2.

Figure 12:
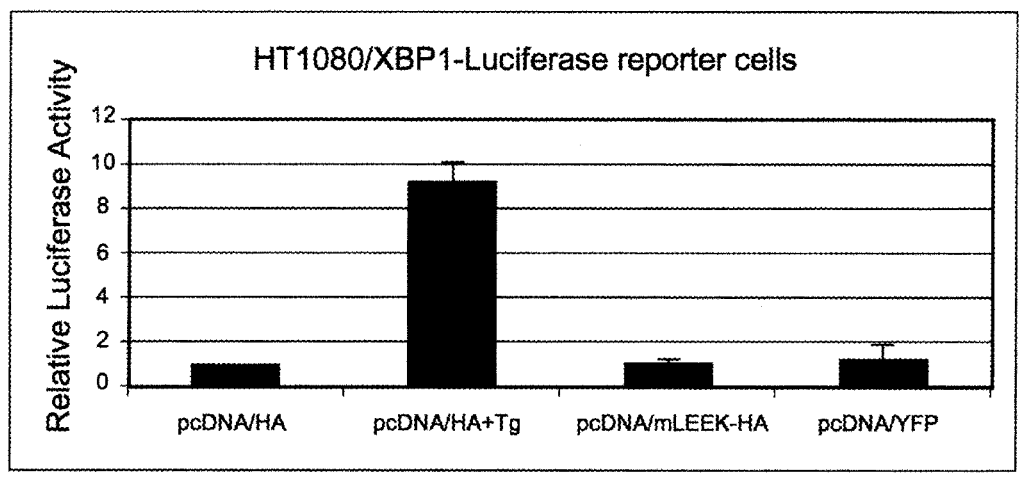
FIG. 12 is a graph showing effects of expression of mLEEK in HT1080 cells containing an XBP-1/luciferase construct cDNA.

Specifically, HT1080 cells containing the cDNA for XBP-1 fused out of frame with the luciferase gene were transfected with either control vector expressing HA peptide only (pcDNA/HA), vector expressing HA tagged mLEEK (pcDNA/mLEEK-HA), or a non-specific protein (pcDNA/YFP) and then assayed after 24 hours. As a positive control, pcDNA/HA cells were treated with 300 nM thapsigargin (Tg) for 24 h. The results are shown in FIG. 12, which shows that the expression of the mLEEK with an HA tag (pcDNA/mLEEK-HA) did not increase activity of the XBP-1/luciferase gene as compared to control plasmid expressing HA tag alone (pcDNA/HA) or YFP (pcDNA/YFP). The use of thapsigargin (Tg) did increase activity of the XBP-1/luciferase gene (pcDNA/HA+Tg). Similar results were seen using 5 ng, 50 ng or 125 ng of DNA in a 96 well plate.

This experiment revealed that the thapsigargin strongly induced XBP-luciferase activity, as expected, but that neither overexpression of mLEEK, YFP, or the HA tag had any effect. Thus, expression of mLEEK does not directly induce XBP-1 cleavage.

To explore if there was a direct effect on the promoters of genes whose expression was increased in response to mLEEK transfection, we obtained promoter constructs for Grp94 and Grp78/BiP driving a luciferase reporter gene. HT1080 cells were seeded into 96 well dishes and transfected with 5 ng of control plasmid (pcDNA/HA) or mLEEK plasmid (pcDNA/mLEEK-HA), which is a concentration of plasmid that is 1/33 to 1/66 less than that used in the microarray experiment. The cells were also transfected with 100 ng of either Grp94 or Grp78/BiP luciferase reporter construct per well. As a positive control, control plasmid cells were also treated with thapsigargin (pcDNA/HA+Tg). The cells were then assayed for luciferase activity after 24 hours.

As shown in FIG. 13, this experiment revealed that expression of mLEEK potently induced transcription from either the Grp94 (FIG. 13A) or Grp78/BiP promoter (FIG. 13B) as compared to control vector, and the extent of induction was greater than that seen with thapsigargin. Expression vectors for YFP or EGFRvIII showed results similar to that of the control vector. Thus, the transcriptional induction seen for Grp94 and Grp78/BiP is specifically due to mLEEK and not simply a function of protein overexpression.

Figure 14:
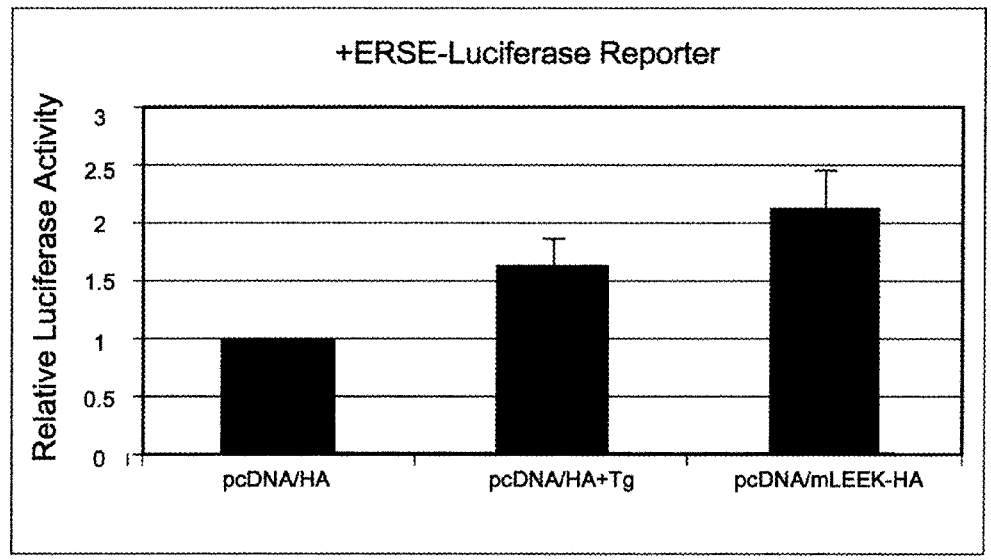
FIG. 14 is a graph showing expression of ERSE-luciferase, from left to right, of a control plasmid, control plasmid cells treated with thapsigargin, and a construct treated with an mLEEK plasmid.

The promoter region of several genes that participate in ER stress have been characterized to have an ER stress response element (ERSE). We obtained a minimal promoter construct that contained a single ERSE element driving the luciferase reporter. HT1080 cells were transfected with 5 ng of control plasmid (pcDNA/HA) or mLEEK plasmid (pcDNA/mLEEK-HA) plus 50 ng of the luciferase reporter construct, containing a single copy of the ERSE, per well of a 96 well dish and then assayed 24 h after transfection. As a positive control, control plasmid cells were also treated with thapsigargin (pcDNA/HA+Tg). The results are shown in FIG. 14. As shown in this graph, the use of thapsigargin (Tg) did increase activity of the luciferase reporter gene (pcDNA/HA+Tg) but the effect seen using mLEEK was greater. The results show that mLEEK was capable of increasing transcription from this reporter element. This data cumulatively suggests that mLEEK has a direct effect on the transcription of both Grp94 and Grp78/BiP, which is mediated via the ERSE present in these promoters.

Thus, the presence of mLEEK may be useful in diagnosing, evaluating or monitoring diseases that are characterized by the endoplasmic reticulum stress response. In addition, the mLEEK protein may be useful in treating or ameliorating diseases where it would be beneficial to enhance the endoplasmic reticulum stress response. Similarly, blocking mLEEK would have a beneficial effect on conditions characterized by an overexpression of mLEEK in the endoplasmic reticulum stress response.

Summary: Therapeutic Applications of Mutant EGFR

The present mutant EGFR polypeptides may be used to stimulate cell growth resulting from activation of the EGFR. EGFR signaling is important in phenotypes such as cell migration, adhesion, and proliferation. Recent reports have suggested that the EGFR pathway mediates two aspects of behavior, diurnal locomotor activity and suppression of locomotion in response to light (masking). Activation of EGFR signaling can play a significant role in wound healing. See, Nakamura et al., "The Epidermal Growth Factor Receptor (EGFR): Role in Corneal Wound Healing and Homeostasis," *Experimental Eye Research*, Volume 72, Number 5, May 2001, pp. 511-517(7).

The present mutant EGFR polypeptides may also be used to treat diseases in which it would be beneficial to enhance the endoplasmic reticulum stress response. Examples of such diseases include, but are not limited to, diabetes, cystic fibrosis, bipolar disorder, neurodegenerative diseases such as Alzheimer's, Huntington's and Parkinson's disease, and conditions of ischemia or hypoxia such as stroke or ischemic heart disease.

The down regulation or interference with mutant EGFR has a potential benefit in a wide variety of tumors. These tumors include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma. Particular tumors include those of the brain, liver, kidney, bladder, breast, gastric, ovarian, colorectal, prostate, pancreatic, breast, lung, vulval, thyroid, colorectal, oesophageal, hepatic carcinomas, sarcomas, glioblastomas, head and neck, leukemias and lymphoid malignancies.

Mutant EGFR may be blocked in a number of ways.

Antibodies may be raised against it in a patient or raised exogenously and administered to a patient. It is known that another EGFR variant, EGFRvIII, is an attractive target for diagnostics and anti-cancer therapy as it creates a unique tumor-specific epitope that is highly expressed in multiple types of cancer. Immunotherapeutic approaches have been shown to be effective in animal models using monoclonal antibodies or fragments directed against EGFRvIII that are 'unarmed', radiolabeled, or conjugated to toxin molecules (Kuan C T, Wikstrand C J, Bigner D, "EGF mutant receptor vIII as a molecular target in cancer therapy," *Endocrine-Related Cancer* 2001; 8:83-96). Vaccine approaches which exploit the immunogenic potential of a 14mer peptide representing the unique EGFRvIII sequence have also demonstrated the ability to produce a diverse and potent anti-tumor response in animal models which has now been translated into a Phase I trial enrolling breast and other cancers and a Phase I trial for glioblastoma that has already shown statistically significant differences in time to progression (Humphrey P A, Wong A J, Vogelstein B, Zalutsky M R, Fuller G N, Archer G E et al., "Anti-synthetic peptide antibody reacting at the fusion junction of deletion-mutant epidermal growth factor receptors in human glioblastoma," *Proc Natl Acad Sci*

USA 1990; 87:4207-4211; Moscatello D K, Ramirez G, Wong A J, "A naturally occurring mutant human epidermal growth factor receptor as a target for peptide vaccine immunotherapy of tumors," *Cancer Res* 1997; 57(8):1419-1424).

Thus, one may prepare a peptide vaccine of a sequence substantially identical to, or identical to the sequence LEEKKGVTVWEL ("mLEEK peptide") (SEQ ID NO: 13), or to the exon 1:24 or exon 1:28 mutant peptides disclosed above. This sequence may be shortened to about 5 to 8 amino acids but will include the amino acids immediately flanking the novel junction (e.g., the mLEEK KG sequence), or lengthened using the sequence of EGFR given here. The substantially pure preparation of polypeptide comprising the amino acid sequence above and its corresponding to the nucleotide sequences can be made using any of the techniques which are known in the art. For example, the Merrifield technique (Journal of American Chemical Society, vol. 85, pp. 2149-2154, 1968) can be used. Substantial purity means that the preparation is greater than 75% free of other proteins normally found in human cells. Preferably the preparation is greater than 90% free of other proteins. Polypeptides may be longer or shorter or have conservative amino acid changes that do not change the epitope(s) found on the peptide that are not found on normal intact EGFR. Polypeptides can be tested to determine if they are able to stimulate mammals to produce antibodies, which are immunoreactive with epitopes found on deletion mutant EGFR, but not found on normal EGFR. Methods of immunizing mammals to stimulate antibody production are well known in the art.

The effect of a vaccine is not limited to the induction of antibodies against mutant EGFR. The vaccine may also elicit T cell responses against cells bearing the mutant EGFR. Moscatello et al., (supra) demonstrated that a vaccine against EGFRvIII not only elicited antibodies against EGFRvIII, but also elicited $CD8^+$ and $CD4^+$ cellular response against cells expressing EGFRvIII and cytotoxic T cell activity against these cells. Thus one would expect, given the present teachings and the state of the art, that the present peptides could be prepared to elicit a similar response in a vaccine.

Methods for testing the immunoreactivity of antibodies for known antigens are also well known. The present vaccines may also be formulated as nucleic acids encoding the immunogenic peptides.

Monoclonal antibodies to mutant EGFR may be prepared by a variety of means and developed as therapies. In one embodiment, the EGFR inhibitor is prepared similar to an antibody such as ERBITUTUX™ (cetuximab, Imclone Systems Inc.) and ABX-EGF™ (panitumumab, Abgenix, Inc.).

A detailed description of a human monoclonal antibody to wild type EGFR is given in US 2005/0100546 by Jakobovits, et al., published May 12, 2005, entitled "Human monoclonal antibodies to epidermal growth factor receptor." Given the present teachings, a human monoclonal antibody may be prepared to mutant EGFR using the approaches described there, namely using human antibody-producing XenoMouse strains to generate potent fully human anti-mutant EGFR MAbs. As previously described, these mouse strains were engineered to be deficient in mouse antibody production and to contain integrated megabase-sized fragments from the human heavy and kappa light chain loci with the majority of the human antibody gene repertoire. Another approach is the "minilocus" approach. In the minilocus approach, an exogenous Ig locus is mimicked through the inclusion of pieces (individual genes) from the Ig locus. Thus, one or more $V_H$ genes, one or more DH genes, one or more $J_H$ genes, a mu constant region, and a second constant region (preferably a gamma constant region) are formed into a construct for insertion into an animal. This approach is described in U.S. Pat. No. 5,545,807 to Surani et al., and U.S. Pat. Nos. 5,545,806 and 5,625,825, both to Lonberg and Kay, and other documents.

A human monoclonal antibody to a mutant EGFR may be characterized in that it binds to a region of the expressed mutant EGFR containing the above-described "mLEEK peptide," or a corresponding peptide in the 1:24 or 1:28 mutant. The antibody further may be characterized in that it inhibits EGFR signaling.

The therapies described in this section may be used in combination with an EGFR inhibitor that is a small molecule that competes with ATP such as TARCEVA™ (erlotinib, OSI Pharmaceuticals), IRESSA™ (gefitinib, Astra-Zeneca), tyrphostins described by Dvir, et al., *J Cell Biol.*, 113:857-865 (1991); tricyclic pyrimidine compounds disclosed in U.S. Pat. No. 5,679,683; and/or compound 6-(2,6-dichlorophenyl)-2-(4-(2-diethylaminoethoxy)phenylamino)-8-methyl-8H-pyrido(2,3-d)pyrimidin-7-one (known as PD166285) disclosed in Panek, et al., *Journal of Pharmacology and Experimental Therapeutics* 283, 1433-1444 (1997).

In addition, subsequences of the mutant EGFR polypeptide subsequences substantially identical to those set forth in SEQ ID NOs: 5, 7, and 9 (either with or without the first 24 amino acids) may be used therapeutically.

The present mutant EGFRs exist as mRNA, which may be blocked by a variety of methods known in the art, including antisense oligonucleotides. Guidance for preparing such molecules is found, e.g., in U.S. Pat. No. 6,071,891 to Low, et al., issued Jun. 6, 2000, entitled "Insulin-like growth factor 1 receptors (IGF-1R) antisense oligonucleotide cells composition." Antisense oligonucleotides are nucleotide sequences that are complementary to specified segments of a targeted gene or mRNA. The binding of an antisense oligonucleotide to DNA or RNA within a cell can inhibit translation or transcription in the cell, which can disrupt gene expression. Typically, antisense oligonucleotides are about 14 to about 25 nucleotides in length, since it is believed that at least about 14 bases are required to specifically target a unique mammalian gene sequence. As described above, siRNA may also be used. Guidance for preparation of molecules for silencing RNA, in addition to that provided above, may be found in U.S. Pat. No. 6,506,559 to Fire, et al., issued Jan. 14, 2003, entitled "Genetic inhibition by double-stranded RNA."

Summary: Diagnostic Applications of Mutant EGFR

As described above, mutant EGFR has been found in tumor cells, but not in normal cells, when these cells were extracted and their mRNA analyzed. The presence of mutant EGFR expression is indicative of a tumorigenic phenotype. The presence of mutant EGFR expression may be detected in a suspected tumor cell with antibodies or with nucleic acid probes. In addition, it has been shown that mutant EGFR is found in cell media, and may be found in the serum. Also, various mutations in EGFR affect clinical outcome. Clinical status may be evaluated by monitoring tumors with EGFR mutations (mLEEK, 1:24, 1:28, and/or EGFR viii) and wild-type EGFR. These can be analyzed according to response (complete+partial) benefit (response+stable disease) and progressive disease. Accordingly, the present invention provides a method for determining the prognosis of a patient having a tumor comprising determining in a sample of said tumor the presence or absence of one or more mLEEK EGFR mutations comprising deletion of exons 2-22 (or the amino acid sequence corresponding to exons 2-22) whereby the presence of said one or more mLEEK EGFR mutation indicates a different prognosis, which may be expected to result in a poor outcome due to constitutive activation of the EGFR activity.

1:24 and 1:28 deletions may be similarly monitored. By "prognosis" is meant response and/or benefit and/or survival. By "EGFR mutations" means an amino acid or nucleic acid sequence that differs from wild-type EGFR protein or nucleic acid respectively found on one allele (heterozygous) or both alleles (homozygous) and may be somatic or germ line, and further is a mutation in an EGFR family member in which the mature peptide comprises a short N terminal sequence (approximately six amino acids) fused directly to a C terminal portion beginning at about amino acid 900 of the full length protein. In a particular embodiment said mutation is found in the kinase domain region (KDR) of EGFR.

Also as described above, mLEEK appears to induce the endoplasmic reticulum stress response. Thus, the presence of mLEEK, as assayed, by example, by antibody, PCR, or RT-PCR may be used to diagnose diseases that are characterized by the endoplasmic reticulum stress response. Such diseases include, but are not limited to, diabetes, cystic fibrosis, bipolar disorder, neurodegenerative diseases such as Alzheimer's, Huntington's and Parkinson's disease, and conditions of ischemia or hypoxia such as stroke or ischemic heart disease.

The nucleotide sequences provided by the invention can be used to form gene probes in accordance with any of the standard techniques. The DNA probes contemplated for use in this invention may be derived from the DNA of cell lines grown in vitro or xenografts maintained in vivo which contain the DNA spanning the deletion site. The size of a DNA probe can vary from approximately 20 nucleotides to hundreds of nucleotides. The DNA probe may be radiolabeled, labeled with a fluorescent material, or the like. Procedures for the preparation and labeling of DNA probes are well known in the art.

The diagnostic test employing a DNA probe will employ a cell sample from an individual who is being screened for the presence of a tumor, including but not limited to breast cancers, lung cancers, and gliomas. Other tumors that harbor EGFR mutations may also be tested. In addition, diseases characterized by the endoplasmic reticulum stress response may be tested. The sample will be isolated from the suspect tissue. DNA is recovered from the cell employing standard techniques well known to those skilled in the art. The DNA is then incubated with a probe under conditions where homologous sequences hybridize but sequences that diverge do not, and hybridization is thereafter detected. Hybridization to a deletion-specific probe indicates the presence of the deletion. Enzymes such as S1 nuclease can be employed to remove portions of a DNA or RNA molecule, which do not hybridize. The size of the duplex nucleic acid that remains can be determined by standard means. Duplexes, which are smaller than the probe, indicate a deletion, rearrangement, or other mismatch. Thus probes, which are useful, may be derived from intact as well as mutant alleles.

Summary: Research Applications of Mutant EGFR and Exon 1-24 and Exon 1-28 Mutants As described above, the present mutant EGFR constructs may be transfected into cells, and their effects studied. Since mutant EGFR and the present variants contain the autophosphorylation domain, but lack the extracellular ligand binding domain, their expression is associated with an abnormal growth phenotype, which is characterized by a constitutively active EGFR receptor.

The substantially pure preparation of polypeptide of the present invention can be used to affinity purify antibodies specific for the mutant EGFR protein. In addition, the preparation of polypeptides of the present invention can be used to stimulate production of antibodies in a mammal to be used as an antibody source by immunizing the mammal with the preparation. Such immunization may optionally employ coupling of the polypeptide to a larger immunogenic substance such as keyhole limpet hemocyanin. For affinity purification of antibodies, the polypeptide can be coupled to an inert matrix, such as agarose beads. Techniques for such coupling are well known in the art. The preparation of the polypeptide can also be used to quantitate antibodies specific for mutant EGFR in an antibody preparation. In such a case, the synthetic peptide will usually be coupled to a larger inert proteinaceous substance such as bovine serum albumin. Once again, the techniques for coupling polypeptides to such matrices are well known in the art.

In addition, as explained in more detail in US 2005/0272083, referenced above, a method of screening for compounds that inhibit signaling of a mutant EGFR protein (1-24 or 1-28 mutant) can be designed, comprising contacting said mutant with a test compound, and detecting a change in the amount of transcription from a luciferase promoter reporter construct, such as, but not limited to, the promoter from c-fos, Grp78/BiP, or Grp94. A reduction of transcription from said reporter construct would indicate that said test compound is an inhibitor of mutant signaling.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

What is claimed is:

1. An isolated antibody specifically binding to a mutant EGFR polypeptide having an extracellular domain less than about 30 amino acids, having a cytoplasmic autophosphorylation domain, and being substantially identical to the amino acid sequence of one of an exon 1:23 fusion polypeptide according to SEQ ID NO: 5, an exon 1:24 fusion polypeptide according to SEQ ID NO: 7, and an exon 1:28 fusion polypeptide according to SEQ ID NO: 9.

2. The antibody of claim 1 which is a monoclonal antibody.

3. The antibody of claim 1 which is an antibody fragment.

4. The antibody of claim 1 which is a polyclonal antibody.

5. The antibody of claim 1 wherein the amino acid sequence of the exon 1:24 fusion polypeptide comprises a sequence LEEKKXWMIDADSR (SEQ ID NO: 10), wherein X is any or no amino acid.

6. The antibody of claim 1 wherein the amino acid sequence of the exon 1:28 fusion polypeptide comprises a sequence LEEKKEYINQSVP (SEQ ID NO: 11).

* * * * *

SEQUENCE LISTING

<160> NUMBER OF SEQ ID NOS: 38

<210> SEQ ID NO 1
<211> LENGTH: 13
<212> TYPE: PRT
<213> ORGANISM: Artificial Sequence
<220> FEATURE:
<223> OTHER INFORMATION: peptide including fusion junction of EGFRvIII

<400> SEQUENCE: 1

Leu Glu Glu Lys Lys Gly Asn Tyr Val Val Thr Asp His
1               5                   10

<210> SEQ ID NO 2
<211> LENGTH: 11
<212> TYPE: PRT
<213> ORGANISM: Artificial Sequence
<220> FEATURE:
<223> OTHER INFORMATION: peptide from EGFRvIII

<400> SEQUENCE: 2

Leu Glu Glu Lys Lys Gly Asn Tyr Val Val Thr
1               5                   10

<210> SEQ ID NO 3
<211> LENGTH: 14
<212> TYPE: PRT
<213> ORGANISM: Artificial Sequence
<220> FEATURE:
<223> OTHER INFORMATION: peptide from EGFRvIII

<400> SEQUENCE: 3

Leu Glu Glu Lys Lys Gly Asn Tyr Val Val Thr Asp His Cys
1               5                   10

<210> SEQ ID NO 4
<211> LENGTH: 2918
<212> TYPE: DNA
<213> ORGANISM: Homo sapiens

<400> SEQUENCE: 4

```
gccgcgctgc gccggagtcc cgagctagcc ccggcgccgc cgccgcccag accggacgac      60
aggccacctc gtcggcgtcc gcccgagtcc ccgcctcgcc gccaacgcca caaccaccgc     120
gcacggcccc ctgactccgt ccagtattga tcgggagagc cggagcgagc tcttcgggga     180
gcagcgatgc gaccctccgg gacgccgggg cagcgctcc tggcgctgct ggctgcgctc     240
tgcccggcga gtcgggctct ggaggaaaag aaagggtga ccgtttggga gttgatgacc     300
tttggatcca agccatatga cggaatccct gccagcgaga tctcctccat cctggagaaa     360
ggagaacgcc tccctcagcc acccatatgt accatcgatg tctacatgat catggtcaag     420
tgctggatga tagacgcaga tagtcgccca agttccgtg agttgatcat cgaattctcc     480
aaaatggccc gagacccca cgctacctt gtcattcagg gggatgaaag aatgcatttg     540
ccaagtccta cagactccaa cttctaccgt gccctgatgg atgaagaaga catggacgac     600
gtggtggatg ccgacgagta cctcatccca cagcagggct tcttcagcag ccctccacg     660 tcacggactc cctcctgag ctctctggtg caaccagcaa caattccacc gtggcttgca     720
ttgatagaaa tgggctgcaa agctgtccca tcaaggaaga cagcttcttg cagcgataca     780
gctcagaccc cacaggcgcc ttgactgagg acagcataga cgacaccttc ctcccagtgc     840
ctgaatacat aaaccagtcc gttcccaaaa ggcccgctgg ctctgtgcag atcctgtct     900 atcacaatca gcctctgaac cccgcgccca gcagagaccc acactaccag gaccccaca     960 gcactgcagt gggcaacccc gagtatctca acactgtcca gcccacctgt gtcaacagca    1020
cattcgacag ccctgccac tgggcccaga aaggcagcca ccaaattagc ctggacaacc    1080
ctgactacca gcaggacttc tttcccaagg aagccaagcc aaatggcatc tttaagggct    1140
ccacagctga aaatgcagaa tacctaaggg tcgcgccaca aagcagtgaa tttattggag    1200
catgaccacg gaggatagta tgagccctaa aaatccagac tctttcgata cccaggacca    1260
```

|  |  |  |  |  |  |
|---|---|---|---|---|---|
| agccacagca | ggtcctccat | cccaacagcc | atgcccgcat | tagctcttag | acccacagac | 1320 |
| tggttttgca | acgtttacac | cgactagcca | ggaagtactt | ccacctcggg | cacattttgg | 1380 |
| gaagttgcat | tcctttgtct | tcaaactgtg | aagcatttac | agaaacgcat | ccagcaagaa | 1440 |
| tattgtccct | ttgagcagaa | atttatcttt | caaagaggta | tatttgaaaa | aaaaaaaaaa | 1500 |
| agtatatgtg | aggattttta | ttgattgggg | atcttggagt | ttttcattgt | cgctattgat | 1560 |
| ttttacttca | atgggctctt | ccaacaagga | agaagcttgc | tggtagcact | tgctaccctg | 1620 |
| agttcatcca | ggcccaactg | tgagcaagga | gcacaagcca | caagtcttcc | agaggatgct | 1680 |
| tgattccagt | ggtctgcctt | caaggcttcc | actgcaaaac | actaaagatc | caagaaggcc | 1740 |
| ttcatggccc | cagcaggccg | gatcggtact | gtatcaagtc | atggcaggta | cagtaggata | 1800 |
| agccactctg | tcccttcctg | ggcaaagaag | aaacggaggg | gatgaattct | tccttagact | 1860 |
| tacttttgta | aaaatgtccc | cacggtactt | actccccact | gatggaccag | tggtttccag | 1920 |
| tcatgagcgt | tagactgact | tgtttgtctt | ccattccatt | gttttgaaac | tcagtatgcc | 1980 |
| gccctgtct | tgctgtcatg | aaatcagcaa | gagaggatga | cacatcaaat | aataactcgg | 2040 |
| attccagccc | acattggatt | catcagcatt | tggaccaata | gcccacagct | gagaatgtgg | 2100 |
| aatacctaag | gataacaccg | cttttgttct | cgcaaaaacg | tatctcctaa | tttgaggctc | 2160 |
| agatgaaatg | catcaggtcc | tttggggcat | agatcagaag | actacaaaaa | tgaagctgct | 2220 |
| ctgaaatctc | ctttagccat | caccccaacc | ccccaaaatt | agtttgtgtt | acttatggaa | 2280 |
| gatagttttc | tccttttact | tcacttcaaa | agctttttac | tcaaagagta | tatgttccct | 2340 |
| ccaggtcagc | tgcccccaaa | ccccctcctt | acgctttgtc | acacaaaaag | tgtctctgcc | 2400 |
| ttgagtcatc | tattcaagca | cttacagctc | tggccacaac | agggcatttt | acaggtgcga | 2460 |
| atgacagtag | cattatgagt | agtgtgaatt | caggtagtaa | atatgaaact | agggtttgaa | 2520 |
| attgataatg | ctttcacaac | atttgcagat | gttttagaag | gaaaaaagtt | ccttcctaaa | 2580 |
| ataatttctc | tacaattgga | agattggaag | attcagctag | ttaggagccc | attttttcct | 2640 |
| aatctgtgtg | tgccctgtaa | cctgactggt | taacagcagt | cctttgtaaa | cagtgtttta | 2700 |
| aactctccta | gtcaatatcc | accccatcca | atttatcaag | gaagaaatgg | ttcagaaaat | 2760 |
| attttcagcc | tacagttatg | ttcagtcaca | cacacataca | aaatgttcct | tttgcttta | 2820 |
| aagtaattt | tgactcccag | atcagtcaga | gcccctacag | cattgttaag | aaagtatttg | 2880 |
| attttgtct | caatgaaaat | aaaactatat | tcatttcc |  |  | 2918 |

<210> SEQ ID NO 5
<211> LENGTH: 338
<212> TYPE: PRT
<213> ORGANISM: Homo sapiens

<400> SEQUENCE: 5

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Val Thr
            20                  25                  30

Trp Glu Leu Met Thr Phe Gly Ser Lys Pro Tyr Asp Gly Ile Pro Ala
        35                  40                  45

Ser Glu Ile Ser Ser Ile Leu Glu Lys Gly Glu Arg Leu Pro Gln Pro
    50                  55                  60

Pro Ile Cys Thr Ile Asp Val Tyr Met Ile Met Val Lys Cys Trp Met
65                  70                  75                  80

```
Ile Asp Ala Asp Ser Arg Pro Lys Phe Arg Glu Leu Ile Ile Glu Phe
             85                  90                  95
Ser Lys Met Ala Arg Asp Pro Gln Arg Tyr Leu Val Ile Gln Gly Asp
         100                 105                 110
Glu Arg Met His Leu Pro Ser Pro Thr Asp Ser Asn Phe Tyr Arg Ala
     115                 120                 125
Leu Met Asp Glu Glu Asp Met Asp Asp Val Val Asp Ala Asp Glu Tyr
 130                 135                 140
Leu Ile Pro Gln Gln Gly Phe Phe Ser Ser Pro Ser Thr Ser Arg Thr
145                 150                 155                 160
Pro Leu Leu Ser Ser Leu Ser Ala Thr Ser Asn Asn Ser Thr Val Ala
             165                 170                 175
Cys Ile Asp Arg Asn Gly Leu Gln Ser Cys Pro Ile Lys Glu Asp Ser
         180                 185                 190
Phe Leu Gln Arg Tyr Ser Ser Asp Pro Thr Gly Ala Leu Thr Glu Asp
     195                 200                 205
Ser Ile Asp Asp Thr Phe Leu Pro Val Pro Glu Tyr Ile Asn Gln Ser
 210                 215                 220
Val Pro Lys Arg Pro Ala Gly Ser Val Gln Asn Pro Val Tyr His Asn
225                 230                 235                 240
Gln Pro Leu Asn Pro Ala Pro Ser Arg Asp Pro His Tyr Gln Asp Pro
             245                 250                 255
His Ser Thr Ala Val Gly Asn Pro Glu Tyr Leu Asn Thr Val Gln Pro
         260                 265                 270
Thr Cys Val Asn Ser Thr Phe Asp Ser Pro Ala His Trp Ala Gln Lys
     275                 280                 285
Gly Ser His Gln Ile Ser Leu Asp Asn Pro Asp Tyr Gln Gln Asp Phe
 290                 295                 300
Phe Pro Lys Glu Ala Lys Pro Asn Gly Ile Phe Lys Gly Ser Thr Ala
305                 310                 315                 320
Glu Asn Ala Glu Tyr Leu Arg Val Ala Pro Gln Ser Ser Glu Phe Ile
             325                 330                 335
Gly Ala

<210> SEQ ID NO 6
<211> LENGTH: 2772
<212> TYPE: DNA
<213> ORGANISM: Homo sapiens

<400> SEQUENCE: 6
gccgcgctgc gccggagtcc cgagctagcc ccggcgccgc cgccgcccag accggacgac    60
aggccacctc gtcggcgtcc gcccgagtcc ccgcctcgcc gccaacgcca caaccaccgc   120
gcacggcccc ctgactccgt ccagtattga tcgggagagc cggagcgagc tcttcgggga   180
gcagcgatgc gaccctccgg gacggccggg gcagcgctcc tggcgctgct ggctgcgctc   240
tgcccggcga gtcgggctct ggaggaaaag aaaggctgga tgatagacgc agatagtcgc   300
ccaaagttcc gtgagttgat catcgaattc tccaaaatgg cccgagaccc cagcgctac    360 cttgtcattc aggggatga agaatgcat ttgccaagtc ctacagactc caacttctac    420
cgtgccctga tggatgaaga agacatggac gacgtggtgg atgccgacga gtacctcatc   480
ccacagcagg gcttcttcag cagcccctcc acgtcacgga ctcccctcct gagctctctg   540
agtgcaacca gcaacaattc caccgtggct tgcattgata gaaatgggct gcaaagctgt   600
cccatcaagg aagacagctt cttgcagcga tacagctcag accccacagg cgccttgact   660
```

```
gaggacagca tagacgacac cttcctccca gtgcctgaat acataaacca gtccgttccc    720
aaaaggcccg ctggctctgt gcagaatcct gtctatcaca atcagcctct gaaccccgcg    780
cccagcagag acccacacta ccaggacccc cacagcactg cagtgggcaa ccccgagtat    840
ctcaacactg tccagcccac ctgtgtcaac agcacattcg acagccctgc ccactgggcc    900
cagaaaggca gccaccaaat tagcctggac aaccctgact accagcagga cttctttccc    960
aaggaagcca agccaaatgg catctttaag ggctccacag ctgaaaatgc agaataccta   1020
agggtcgcgc cacaaagcag tgaatttatt ggagcatgac cacggaggat agtatgagcc   1080
ctaaaaatcc agactctttc gatacccagg accaagccac agcaggtcct ccatcccaac   1140
agccatgccc gcattagctc ttagacccac agactggttt tgcaacgttt acaccgacta   1200
gccaggaagt acttccacct cgggcacatt ttgggaagtt gcattccttt gtcttcaaac   1260
tgtgaagcat ttacagaaac gcatccagca agaatattgt ccctttgagc agaaatttat   1320
ctttcaaaga ggtatatttg aaaaaaaaaa aaaagtata tgtgaggatt tttattgatt    1380
ggggatcttg gagttttttca ttgtcgctat tgattttttac ttcaatgggc tcttccaaca   1440
aggaagaagc ttgctggtag cacttgctac cctgagttca tccaggccca actgtgagca   1500
aggagcacaa gccacaagtc ttccagagga tgcttgattc cagtggttct gcttcaaggc   1560
ttccactgca aaacactaaa gatccaagaa ggccttcatg gccccagcag gccggatcgg   1620
tactgtatca agtcatggca ggtacagtag gataagccac tctgtccctt cctgggcaaa   1680
gaagaaacgg agggggatgaa ttcttcctta gacttacttt tgtaaaaatg tccccacggt   1740
acttactccc cactgatgga ccagtggttt ccagtcatga gcgttagact gacttgtttg   1800
tcttccattc cattgttttg aaactcagta tgccgcccct gtcttgctgt catgaaatca   1860
gcaagagagg atgacacatc aaataataac tcggattcca gcccacattg gattcatcag   1920
catttggacc aatagcccac agctgagaat gtggaatacc taaggataac accgcttttg   1980
ttctcgcaaa aacgtatctc ctaatttgag gctcagatga aatgcatcag gtcctttggg   2040
gcatagatca gaagactaca aaaatgaagc tgctctgaaa tctcctttag ccatcacccc   2100
aaccccccaa aattagtttg tgttacttat ggaagatagt tttctccttt tacttcactt   2160
caaaagcttt ttactcaaag agtatatgtt ccctccaggt cagctgcccc caaaccccct   2220
ccttacgctt tgtcacacaa aaagtgtctc tgccttgagc catctattca agcacttaca   2280
gctctggcca caacagggca ttttacaggt gcgaatgaca gtagcattat gagtagtgtg   2340
aattcaggta gtaaatatga aactagggtt tgaaattgat aatgctttca caacatttgc   2400
agatgtttta gaaggaaaaa agttccttcc taaaataatt tctctacaat tggaagattg   2460
gaagattcag ctagttagga gcccattttt tcctaatctg tgtgtgccct gtaacctgac   2520
tggttaacag cagtcctttg taaacagtgt tttaaactct cctagtcaat atccacccca   2580
tccaatttat caaggaagaa atggttcaga aaatattttc agcctacagt tatgttcagt   2640
cacacacaca tacaaaatgt tccttttgct tttaaagtaa tttttgactc ccagatcagt   2700
cagagcccct acagcattgt taagaaagta tttgattttt gtctcaatga aaataaaact   2760
atattcattt cc                                                       2772
```

<210> SEQ ID NO 7
<211> LENGTH: 290
<212> TYPE: PRT
<213> ORGANISM: Homo sapiens

<400> SEQUENCE: 7

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Trp Met
            20                  25                  30

Ile Asp Ala Asp Ser Arg Pro Lys Phe Arg Glu Leu Ile Ile Glu Phe
        35                  40                  45

Ser Lys Met Ala Arg Asp Pro Gln Arg Tyr Leu Val Ile Gln Gly Asp
    50                  55                  60

Glu Arg Met His Leu Pro Ser Pro Thr Asp Ser Asn Phe Tyr Arg Ala
65              70                  75                  80

Leu Met Asp Glu Glu Asp Met Asp Val Val Asp Ala Asp Glu Tyr
                85                  90                  95

Leu Ile Pro Gln Gln Gly Phe Phe Ser Ser Pro Ser Thr Ser Arg Thr
            100                 105                 110

Pro Leu Leu Ser Ser Leu Ser Ala Thr Ser Asn Asn Ser Thr Val Ala
            115                 120                 125

Cys Ile Asp Arg Asn Gly Leu Gln Ser Cys Pro Ile Lys Glu Asp Ser
    130                 135                 140

Phe Leu Gln Arg Tyr Ser Ser Asp Pro Thr Gly Ala Leu Thr Glu Asp
145                 150                 155                 160

Ser Ile Asp Asp Thr Phe Leu Pro Val Pro Glu Tyr Ile Asn Gln Ser
                165                 170                 175

Val Pro Lys Arg Pro Ala Gly Ser Val Gln Asn Pro Val Tyr His Asn
            180                 185                 190

Gln Pro Leu Asn Pro Ala Pro Ser Arg Asp Pro His Tyr Gln Asp Pro
        195                 200                 205

His Ser Thr Ala Val Gly Asn Pro Glu Tyr Leu Asn Thr Val Gln Pro
    210                 215                 220

Thr Cys Val Asn Ser Thr Phe Asp Ser Pro Ala His Trp Ala Gln Lys
225                 230                 235                 240

Gly Ser His Gln Ile Ser Leu Asp Asn Pro Asp Tyr Gln Gln Asp Phe
                245                 250                 255

Phe Pro Lys Glu Ala Lys Pro Asn Gly Ile Phe Lys Gly Ser Thr Ala
            260                 265                 270

Glu Asn Ala Glu Tyr Leu Arg Val Ala Pro Gln Ser Ser Glu Phe Ile
        275                 280                 285

Gly Ala
    290

<210> SEQ ID NO 8
<211> LENGTH: 2349
<212> TYPE: DNA
<213> ORGANISM: Homo sapiens

<400> SEQUENCE: 8
gccgcgctgc gccggagtcc cgagctagcc ccggcgccgc cgccgcccag accggacgac      60
aggccacctc gtcggcgtcc gcccgagtcc ccgcctcgcc gccaacgcca caaccaccgc     120
gcacggcccc ctgactccgt ccagtattga tcggagagag cggagcgagc tcttcgggga     180
gcagcgatgc gacccteegg gacggccggg gcagcgctcc tggcgctgct ggctgcgctc     240 tgccggcga gtcgggctct ggaggaaaag aaagaataca taaccagtc cgttcccaaa      300 aggcccgctg gctctgtgca gaatcctgtc tatcacaatc agcctctgaa ccccgcgccc     360

-continued

```
agcagagacc cacactacca ggaccccac  agcactgcag tgggcaaccc cgagtatctc    420
aacactgtcc agcccacctg tgtcaacagc acattcgaca gccctgccca ctgggcccag    480
aaaggcagcc accaaattag cctggacaac cctgactacc agcaggactt ctttcccaag    540
gaagccaagc caaatggcat ctttaagggc tccacagctg aaaatgcaga atacctaagg    600
gtcgcgccac aaagcagtga atttattgga gcatgaccac ggaggatagt atgagcccta    660
aaaatccaga ctctttcgat acccaggacc aagccacagc aggtcctcca tcccaacagc    720
catgcccgca ttagctctta gacccacaga ctggttttgc aacgtttaca ccgactagcc    780
aggaagtact tccacctcgg gcacattttg ggaagttgca ttcctttgtc ttcaaactgt    840
gaagcattta cagaaacgca tccagcaaga atattgtccc tttgagcaga aatttatctt    900
tcaaagaggt atatttgaaa aaaaaaaaa  aagtatatgt gaggatttt  attgattggg    960
gatcttggag tttttcattg tcgctattga tttttacttc aatgggctct tccaacaagg   1020
aagaagcttg ctggtagcac ttgctaccct gagttcatcc aggcccaact gtgagcaagg   1080
agcacaagcc acaagtcttc cagaggatgc ttgattccag tggttctgct tcaaggcttc   1140
cactgcaaaa cactaaagat ccagaaggc  cttcatggcc ccagcaggcc ggatcggtac   1200
tgtatcaagt catggcaggt acagtaggat aagccactct gtcccttcct gggcaaagaa   1260
gaaacggagg ggatgaattc ttccttagac ttacttttgt aaaaatgtcc ccacggtact   1320
tactccccac tgatggacca gtggtttcca gtcatgagcg ttagactgac ttgtttgtct   1380
tccattccat tgttttgaaa ctcagtatgc cgccctgtc  ttgctgtcat gaaatcagca   1440
agagaggatg acacatcaaa taataactcg gattccagcc cacattggat tcatcagcat   1500
ttggaccaat agcccacagc tgagaatgtg gaatacctaa ggataacacc gcttttgttc   1560
tcgcaaaaac gtatctccta atttgaggct cagatgaaat gcatcaggtc ctttggggca   1620
tagatcagaa gactacaaaa atgaagctgc tctgaaatct cctttagcca tcaccccaac   1680
cccccaaaat tagtttgtgt tacttatgga agatagtttt ctccttttac ttcacttcaa   1740
aagctttta  ctcaaagagt atatgttccc tccaggtcag ctgcccccaa acccctcct   1800
tacgctttgt cacacaaaaa gtgtctctgc cttgagtcat ctattcaagc acttacagct   1860
ctggccacaa cagggcattt tacaggtgcg aatgacagta gcattatgag tagtgtgaat   1920
tcaggtagta aatatgaaac tagggtttga aattgataat gctttcacaa catttgcaga   1980
tgttttagaa ggaaaaaagt tccttcctaa ataatttct  ctacaattgg aagattggaa   2040
gattcagcta gttaggagcc catttttcc  taatctgtgt gtgccctgta acctgactgg   2100
ttaacagcag tcctttgtaa acagtgtttt aaactctcct agtcaatatc caccccatcc   2160
aatttatcaa ggaagaaatg gttcagaaaa tattttcagc ctacagttat gttcagtcac   2220
acacacatac aaaatgttcc ttttgctttt aaagtaattt ttgactccca gatcagtcag   2280
agccccctaca gcattgttaa gaaagtattt gattttgtc  tcaatgaaaa taaaactata   2340
ttcatttcc                                                           2349
```

<210> SEQ ID NO 9
<211> LENGTH: 149
<212> TYPE: PRT
<213> ORGANISM: Homo sapiens

<400> SEQUENCE: 9

```
Met Arg Pro Ser Gly Thr Ala Gly Ala Ala Leu Leu Ala Leu Leu Ala
1               5                   10                  15
```

-continued

```
Ala Leu Cys Pro Ala Ser Arg Ala Leu Glu Glu Lys Lys Glu Tyr Ile
            20                  25                  30

Asn Gln Ser Val Pro Lys Arg Pro Ala Gly Ser Val Gln Asn Pro Val
        35                  40                  45

Tyr His Asn Gln Pro Leu Asn Pro Ala Pro Ser Arg Asp Pro His Tyr
    50                  55                  60

Gln Asp Pro His Ser Thr Ala Val Gly Asn Pro Glu Tyr Leu Asn Thr
65                  70                  75                  80

Val Gln Pro Thr Cys Val Asn Ser Thr Phe Asp Ser Pro Ala His Trp
                85                  90                  95

Ala Gln Lys Gly Ser His Gln Ile Ser Leu Asp Asn Pro Asp Tyr Gln
            100                 105                 110

Gln Asp Phe Phe Pro Lys Glu Ala Lys Pro Asn Gly Ile Phe Lys Gly
        115                 120                 125

Ser Thr Ala Glu Asn Ala Glu Tyr Leu Arg Val Ala Pro Gln Ser Ser
    130                 135                 140

Glu Phe Ile Gly Ala
145

<210> SEQ ID NO 10
<211> LENGTH: 14
<212> TYPE: PRT
<213> ORGANISM: Artificial Sequence
<220> FEATURE:
<223> OTHER INFORMATION: peptide characterizing alteration in 1:24
      mutant
<220> FEATURE:
<221> NAME/KEY: misc_feature
<222> LOCATION: (6)..(6)
<223> OTHER INFORMATION: Xaa can be any naturally occurring amino acid

<400> SEQUENCE: 10

Leu Glu Glu Lys Lys Xaa Trp Met Ile Asp Ala Asp Ser Arg
1               5                   10

<210> SEQ ID NO 11
<211> LENGTH: 13
<212> TYPE: PRT
<213> ORGANISM: Artificial Sequence
<220> FEATURE:
<223> OTHER INFORMATION: peptide characterizing alteration in 1:28
      mutant

<400> SEQUENCE: 11

Leu Glu Glu Lys Lys Glu Tyr Ile Asn Gln Ser Val Pro
1               5                   10

<210> SEQ ID NO 12
<211> LENGTH: 58
<212> TYPE: PRT
<213> ORGANISM: Artificial Sequence
<220> FEATURE:
<223> OTHER INFORMATION: peptide characterizing alteration in mLEEK
<220> FEATURE:
<221> NAME/KEY: misc_feature
<222> LOCATION: (29)..(29)
<223> OTHER INFORMATION: Xaa can be any naturally occurring amino acid

<400> SEQUENCE: 12

Met Arg Pro Ser Gly Thr Ala Gly Ala Ala Leu Leu Ala Leu Leu Ala
1               5                   10                  15

Leu Cys Pro Ala Ser Arg Ala Leu Glu Glu Lys Lys Xaa Val Thr Val
            20                  25                  30
```

```
Trp Glu Leu Met Thr Phe Gly Ser Lys Pro Tyr Asp Gly Ile Pro Ala
                35                  40                  45

Ser Glu Ile Ser Ser Ile Leu Glu Lys Gly
    50                  55

<210> SEQ ID NO 13
<211> LENGTH: 12
<212> TYPE: PRT
<213> ORGANISM: Artificial Sequence
<220> FEATURE:
<223> OTHER INFORMATION: peptide characterizing alteration in mLEEK

<400> SEQUENCE: 13

Leu Glu Glu Lys Lys Gly Val Thr Val Trp Glu Leu
1               5                  10

<210> SEQ ID NO 14
<211> LENGTH: 1210
<212> TYPE: PRT
<213> ORGANISM: Homo sapiens

<400> SEQUENCE: 14

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
```

-continued

```
                    275                 280                 285
Ala Thr Cys Val Lys Lys Cys Pro Arg Asn Tyr Val Thr Asp His
    290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
                355                 360                 365
Leu His Ile Leu Pro Val Ala Phe Arg Gly Asp Ser Phe Thr His Thr
    370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
His Gly Gln Phe Ser Leu Ala Val Val Ser Leu Asn Ile Thr Ser Leu
                435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
                500                 505                 510
Glu Gly Cys Trp Gly Pro Glu Pro Arg Asp Cys Val Ser Cys Arg Asn
                515                 520                 525
Val Ser Arg Gly Arg Glu Cys Val Asp Lys Cys Lys Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
                580                 585                 590
Lys Thr Cys Pro Ala Gly Val Met Gly Glu Asn Asn Thr Leu Val Trp
                595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
                675                 680                 685
Val Glu Pro Leu Thr Pro Ser Gly Glu Ala Pro Asn Gln Ala Leu Leu
    690                 695                 700
```

```
Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
        740                 745                 750

Pro Lys Ala Asn Lys Glu Ile Leu Asp Glu Ala Tyr Val Met Ala Ser
    755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
        820                 825                 830

Leu Val His Arg Asp Leu Ala Ala Arg Asn Val Leu Val Lys Thr Pro
    835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
        900                 905                 910

Lys Pro Tyr Asp Gly Ile Pro Ala Ser Glu Ile Ser Ser Ile Leu Glu
    915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
            965                 970                 975

Arg Tyr Leu Val Ile Gln Gly Asp Glu Arg Met His Leu Pro Ser Pro
        980                 985                 990

Thr Asp Ser Asn Phe Tyr Arg Ala  Leu Met Asp Glu Glu  Asp Met Asp
    995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110
```

```
Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 15
<211> LENGTH: 1210
<212> TYPE: PRT
<213> ORGANISM: Homo sapiens

<400> SEQUENCE: 15

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270
```

-continued

```
Thr Thr Tyr Gln Met Asp Val Asn Pro Glu Gly Lys Tyr Ser Phe Gly
    275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
                355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                    405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
    435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                    485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
    515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
    675                 680                 685
```

```
Val Glu Pro Leu Thr Pro Ser Gly Glu Ala Pro Asn Gln Ala Leu Leu
    690                 695                 700

Arg Ile Leu Lys Glu Thr Glu Phe Lys Ile Lys Val Leu Gly Ser
705                 710                 715                 720

Gly Ala Phe Gly Thr Val Tyr Lys Gly Leu Trp Ile Pro Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
                755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
                995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
```

```
          1100                1105                1110
Pro Leu Asn Pro Ala Pro Ser Arg Asp Pro His Tyr Gln Asp Pro
        1115                1120                1125

His Ser Thr Ala Val Gly Asn Pro Glu Tyr Leu Asn Thr Val Gln
        1130                1135                1140

Pro Thr Cys Val Asn Ser Thr Phe Asp Ser Pro Ala His Trp Ala
        1145                1150                1155

Gln Lys Gly Ser His Gln Ile Ser Leu Asp Asn Pro Asp Tyr Gln
        1160                1165                1170

Gln Asp Phe Phe Pro Lys Glu Ala Lys Pro Asn Gly Ile Phe Lys
        1175                1180                1185

Gly Ser Thr Ala Glu Asn Ala Glu Tyr Leu Arg Val Ala Pro Gln
        1190                1195                1200

Ser Ser Glu Phe Ile Gly Ala
        1205                1210
```

<210> SEQ ID NO 16
<211> LENGTH: 35
<212> TYPE: DNA
<213> ORGANISM: Artificial Sequence
<220> FEATURE:
<223> OTHER INFORMATION: nucleotide sequence characterizing alteration
      in mLEEK

<400> SEQUENCE: 16
ctggaggaaa agaaaggggt gaccgtttgg gagtt                              35

<210> SEQ ID NO 17
<211> LENGTH: 36
<212> TYPE: DNA
<213> ORGANISM: Artificial Sequence
<220> FEATURE:
<223> OTHER INFORMATION: nucleotide sequence characterizing alteration
      in 1:24 mutant

<400> SEQUENCE: 17
ctggaggaaa agaaaggctg gatgatagac gcagat                             36

<210> SEQ ID NO 18
<211> LENGTH: 36
<212> TYPE: DNA
<213> ORGANISM: Artificial Sequence
<220> FEATURE:
<223> OTHER INFORMATION: nucleotide sequence characterizing alteration
      in 1:28 mutant

<400> SEQUENCE: 18
ctggaggaaa agaaagaata cataaaccag tccgtt                             36

<210> SEQ ID NO 19
<211> LENGTH: 21
<212> TYPE: DNA
<213> ORGANISM: Artificial Sequence
<220> FEATURE:
<223> OTHER INFORMATION: forward primer EGFR 176-196

<400> SEQUENCE: 19
ggggagcagc gatgcgaccc t                                             21

<210> SEQ ID NO 20
<211> LENGTH: 21
<212> TYPE: DNA
<213> ORGANISM: Artificial Sequence
<220> FEATURE:
<223> OTHER INFORMATION: reverse primer EGFR 3877-3857

<400> SEQUENCE: 20
gcttggtcct gggtatcgaa a                                              21

<210> SEQ ID NO 21
<211> LENGTH: 221
<212> TYPE: DNA
<213> ORGANISM: Artificial Sequence
<220> FEATURE:
<223> OTHER INFORMATION: antisense RNA probe spanning the exon 1-23
      junction in mLEEK

<400> SEQUENCE: 21
taatacgact cactataggg aggaggcgtt ctcctttctc cagggatgga ggagatctcg    60
ctggcaggat tccgtcatat ggcttggatc caaaggtcat caactcccaa acggtcaccc   120
ctttcttttc ctccagagcc cgactcgccg ggcagagcgc agccagcagc gccaggagcg   180
ctgccccggc cgtgccccgg gttctatagt gtcacctaaa t                       221

<210> SEQ ID NO 22
<211> LENGTH: 13
<212> TYPE: PRT
<213> ORGANISM: Artificial Sequence
<220> FEATURE:
<223> OTHER INFORMATION: peptide corresponding to the mLEEK junction
      including extra cysteine at C-terminus

<400> SEQUENCE: 22

Leu Glu Glu Lys Lys Gly Val Thr Val Trp Glu Leu Cys
1               5                   10

<210> SEQ ID NO 23
<211> LENGTH: 21
<212> TYPE: DNA
<213> ORGANISM: Artificial Sequence
<220> FEATURE:
<223> OTHER INFORMATION: reverse primer EGFR 3012-2992

<400> SEQUENCE: 23
atcgatggta catatgggtg g                                              21

<210> SEQ ID NO 24
<211> LENGTH: 21
<212> TYPE: DNA
<213> ORGANISM: Artificial Sequence
<220> FEATURE:
<223> OTHER INFORMATION: forward nested primer EGFR  202-222

<400> SEQUENCE: 24
acggccgggg cagcgctcct g                                              21

<210> SEQ ID NO 25
<211> LENGTH: 21
<212> TYPE: DNA
<213> ORGANISM: Artificial Sequence
<220> FEATURE:
<223> OTHER INFORMATION: reverse nested primer EGFR 2984-2964

<400> SEQUENCE: 25
aggcgttctc ctttctccag g                                              21

<210> SEQ ID NO 26
<211> LENGTH: 21

-continued

```
<212> TYPE: DNA
<213> ORGANISM: Artificial Sequence
<220> FEATURE:
<223> OTHER INFORMATION: siRNA target

<400> SEQUENCE: 26
aaaagaaagg ggtgaccgtt t                                            21

<210> SEQ ID NO 27
<211> LENGTH: 21
<212> TYPE: DNA
<213> ORGANISM: Artificial Sequence
<220> FEATURE:
<223> OTHER INFORMATION: siRNA target

<400> SEQUENCE: 27
aagaaagggg tgaccgtttg g                                            21

<210> SEQ ID NO 28
<211> LENGTH: 21
<212> TYPE: DNA
<213> ORGANISM: Artificial Sequence
<220> FEATURE:
<223> OTHER INFORMATION: siRNA target

<400> SEQUENCE: 28 aaagggtga ccgtttggga g                                             21

<210> SEQ ID NO 29
<211> LENGTH: 24
<212> TYPE: DNA
<213> ORGANISM: Artificial Sequence
<220> FEATURE:
<223> OTHER INFORMATION: mouse cfos primer cFOS 173-196

<400> SEQUENCE: 29
gctgcaccct cagagttggc tgca                                         24

<210> SEQ ID NO 30
<211> LENGTH: 24
<212> TYPE: DNA
<213> ORGANISM: Artificial Sequence
<220> FEATURE:
<223> OTHER INFORMATION: mouse cfos primer cFOS 697-674

<400> SEQUENCE: 30
aagtttgggg aaagcccggc aagg                                         24

<210> SEQ ID NO 31
<211> LENGTH: 14
<212> TYPE: PRT
<213> ORGANISM: Artificial Sequence
<220> FEATURE:
<223> OTHER INFORMATION: peptide characterizing 1:24 mutant

<400> SEQUENCE: 31

Leu Glu Glu Lys Lys Gly Trp Met Ile Asp Ala Asp Ser Arg
1               5                   10

<210> SEQ ID NO 32
<211> LENGTH: 5531
<212> TYPE: DNA
<213> ORGANISM: Homo sapiens

<400> SEQUENCE: 32
gccgcgctgc gccggagtcc cgagctagcc ccggcgccgc cgccgcccag accggacgac    60
```

```
aggccacctc gtcggcgtcc gcccgagtcc ccgcctcgcc gccaacgcca caaccaccgc   120
gcacggcccc ctgactccgt ccagtattga tcgggagagc cggagcgagc tcttcgggga   180
gcagcgatgc gaccctccgg gacggccggg gcagcgctcc tggcgctgct ggctgcgctc   240
tgcccggcga gtcgggctct ggaggaaaag aaagtttgcc aaggcacgag taacaagctc   300
acgcagttgg gcacttttga agatcatttt ctcagcctcc agaggatgtt caataactgt   360
gaggtggtcc ttgggaattt ggaaattacc tatgtgcaga ggaattatga tctttccttc   420
ttaaagacca tccaggaggt ggctggttat gtcctcattg ccctcaacac agtggagcga   480
attcctttgg aaaacctgca gatcatcaga ggaaatatgt actacgaaaa ttcctatgcc   540
ttagcagtct tatctaacta tgatgcaaat aaaaccggac tgaaggagct gcccatgaga   600
aatttacagg aaatcctgca tggcgccgtg cggttcagca caaaccctgc cctgtgcaac   660
gtggagagca tccagtggcg ggacatagtc agcagtgact ttctcagcaa catgtcgatg   720
gacttccaga accacctggg cagctgccaa agtgtgatcc aagctgtcc caatgggagc   780 tgctggggtg caggagagga gaactgccag aaactgacca aaatcatctg tgcccagcag   840
tgctccgggc gctgccgtgg caagtccccc agtgactgct gccacaacca gtgtgctgca   900
ggctgcacag gcccccggga gagcgactgc ctggtctgcc gcaaattccg agacgaagcc   960
acgtgcaagg acacctgccc cccactcatg ctctacaacc ccaccacgta ccagatggat  1020 gtgaacccg agggcaaata cagctttggt gccacctgcg tgaagaagtg tccccgtaat  1080
tatgtggtga cagatcacgg ctcgtgcgtc cgagcctgtg gggccgacag ctatgagatg  1140
gaggaagacg gcgtccgcaa gtgtaagaag tgcgaagggc cttgccgcaa agtgtgtaac  1200
ggaataggta ttggtgaatt taaagactca ctctccataa atgctacgaa tattaaacac  1260
ttcaaaaact gcacctccat cagtggcgat ctccacatcc tgccggtggc atttaggggt  1320
gactccttca cacatactcc tcctctggat ccacaggaac tggatattct gaaaaccgta  1380
aaggaaatca cagggttttt gctgattcag gcttggcctg aaaacaggac ggacctccat  1440
gcctttgaga acctagaaat catacgcggc aggaccaagc aacatggtca gttttctctt  1500
gcagtcgtca gcctgaacat aacatccttg ggattacgct ccctcaagga gataagtgat  1560
ggagatgtga taatttcagg aaacaaaaat ttgtgctatg caaatacaat aaactggaaa  1620
aaactgtttg gacctccggg tcagaaaacc aaaattataa gcaacagagg tgaaaacagc  1680
tgcaaggcca caggccaggt ctgccatgcc ttgtgctccc ccgagggctg ctggggcccg  1740
gagcccaggg actgcgtctc ttgccggaat gtcagccgag gcagggaatg cgtggacaag  1800
tgcaagcttc tggagggtga gccaagggag tttgtggaga actctgagtg catacagtgc  1860
cacccagagt gcctgcctca ggccatgaac atccctgca caggacgggg accagacaac  1920
tgtatccagt gtgcccacta cattgacggc ccccactgcg tcaagacctg cccggcagga  1980
gtcatgggag aaaacaacac cctggtctgg aagtacgcag acgccggcca tgtgtgccac  2040
ctgtgccatc caaactgcac ctacggatgc actgggccag gtcttgaagg ctgtccaacg  2100
aatgggccta agatcccgtc catcgccact gggatggtgg gggccctcct cttgctgctg  2160
gtggtggccc tggggatcgg cctcttcatg cgaaggcgcc acatcgttcg gaagcgcacg  2220
ctgcggaggc tgctgcagga gagggagctt gtggagcctc ttacacccag tggagaagct  2280
cccaaccaag ctctcttgag gatcttgaag gaaactgaat tcaaaaagat caaagtgctg  2340
ggctccggtg cgttcggcac ggtgtataag ggactctgga tcccagaagg tgagaaagtt  2400
```

```
aaaattcccg tcgctatcaa ggaattaaga gaagcaacat ctccgaaagc caacaaggaa    2460
atcctcgatg aagcctacgt gatggccagc gtggacaacc cccacgtgtg ccgcctgctg    2520
ggcatctgcc tcacctccac cgtgcaactc atcacgcagc tcatgcccttt cggctgcctc   2580
ctggactatg tccgggaaca caaagacaat attggctccc agtacctgct caactggtgt    2640
gtgcagatcg caaagggcat gaactacttg gaggaccgtc gcttggtgca ccgcgacctg    2700
gcagccagga acgtactggt gaaaacaccg cagcatgtca agatcacaga ttttgggctg    2760
gccaaactgc tgggtgcgga agagaaagaa taccatgcag aaggaggcaa agtgcctatc    2820
aagtggatgg cattggaatc aattttacac agaatctata cccaccagag tgatgtctgg    2880
agctacgggg tgaccgttg ggagttgatg acctttggat ccaagccata tgacggaatc    2940
cctgccagcg agatctcctc catcctggag aaaggagaac gcctcccctca gccacccata   3000
tgtaccatcg atgtctacat gatcatggtc aagtgctgga tgatagacgc agatagtcgc    3060
ccaaagttcc gtgagttgat catcgaattc tccaaaatgg cccgagaccc ccagcgctac    3120
cttgtcattc aggggggatga agaatgcat ttgccaagtc ctacagactc caacttctac     3180
cgtgccctga tggatgaaga agacatggac gacgtggtgg atgccgacga gtacctcatc    3240
ccacagcagg gcttcttcag cagcccctcc acgtcacgga ctcccctcct gagctctctg    3300
agtgcaaacca gcaacaattc caccgtggct tgcattgata gaaatgggct gcaaagctgt    3360
cccatcaagg aagacagctt cttgcagcga tacagctcag accccacagg cgccttgact    3420
gaggacagca tagacgacac cttcctccca gtgcctgaat acataaacca gtccgttccc    3480
aaaaggcccg ctggctctgt gcagaatcct gtctatcaca atcagcctct gaaccccgcg    3540
cccagcagag acccacacta ccaggacccc cacagcactg cagtgggcaa ccccgagtat    3600
ctcaacactg tccagcccac ctgtgtcaac agcacattcg acagccctgc ccactgggcc    3660
cagaaaggca gccaccaaat tagcctggac aaccctgact accagcagga cttcttttccc   3720
aaggaagcca agccaaatgg catctttaag ggctccacag ctgaaaatgc agaataccta    3780
agggtcgcgc cacaaagcag tgaatttatt ggagcatgac cacggaggat agtatgagcc    3840
ctaaaaatcc agactctttc gatacccagg accaagccac agcaggtcct ccatcccaac    3900
agccatgccc gcattagctc ttagacccac agactggttt tgcaacgttt acaccgacta    3960
gccaggaagt acttccacct cgggcacatt ttgggaagtt gcattccttt gtcttcaaac    4020
tgtgaagcat ttacagaaac gcatccagca agaatattgt cccttttgagc agaaatttat    4080
ctttcaaaga ggtatatttg aaaaaaaaaa aaaagtata tgtgaggatt tttattgatt      4140
ggggatcttg gagttttca ttgtcgctat tgatttttac ttcaatgggc tcttccaaca     4200
aggaagaagc ttgctggtag cacttgctac cctgagttca tccaggccca actgtgagca    4260
aggagcacaa gccacaagtc ttccagagga tgcttgattc cagtggttct gcttcaaggc    4320
ttccactgca aaacactaaa gatccaagaa ggccttcatg gccccagcag gccggatcgg    4380
tactgtatca agtcatggca ggtacagtag gataagccac tctgtccctt cctgggcaaa    4440
gaagaaacgg aggggatgaa ttcttcctta gacttacttt tgtaaaaatg tccccacggt    4500
acttactccc cactgatgga ccagtggttt ccagtcatga gcgttagact gacttgtttg    4560
tcttccattc cattgttttg aaactcagta tgccgcccct gtcttgctgt catgaaatca    4620
gcaagagagg atgacacatc aaataataac tcggattcca gcccacattg gattcatcag    4680
catttggacc aatagcccac agctgagaat gtggaatacc taaggataac accgcttttg    4740
ttctcgcaaa aacgtatctc ctaatttgag gctcagatga aatgcatcag gtccctttggg  4800
```

```
gcatagatca gaagactaca aaaatgaagc tgctctgaaa tctcctttag ccatcacccc    4860
aaccccccaa aattagtttg tgttactat ggaagatagt tttctccttt tacttcactt    4920
caaaagcttt ttactcaaag agtatatgtt ccctccaggt cagctgcccc caaaccccct   4980
ccttacgctt tgtcacacaa aaagtgtctc tgccttgagt catctattca agcacttaca    5040
gctctggcca acagggca ttttacaggt gcgaatgaca gtagcattat gagtagtgtg     5100
aattcaggta gtaaatatga aactagggtt tgaaattgat aatgctttca caacatttgc    5160
agatgtttta gaaggaaaaa agttccttcc taaaataatt tctctacaat tggaagattg    5220
gaagattcag ctagttagga gcccatttt tcctaatctg tgtgtgccct gtaacctgac     5280
tggttaacag cagtcctttg taaacagtgt tttaaactct cctagtcaat atccaccccca   5340 tccaatttat caaggaagaa atggttcaga aaatattttc agcctacagt tatgttcagt    5400
cacacacaca tacaaaatgt tccttttgct tttaaagtaa ttttgactc ccagatcagt     5460 cagagcccct acagcattgt taagaaagta tttgattttt gtctcaatga aaataaaact   5520
atattcattt c                                                         5531
```

<210> SEQ ID NO 33
<211> LENGTH: 60
<212> TYPE: PRT
<213> ORGANISM: Artificial Sequence
<220> FEATURE:
<223> OTHER INFORMATION: peptide characterizing 1:24 mutant

<400> SEQUENCE: 33

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Trp Met Ile
            20                  25                  30

Asp Ala Asp Ser Arg Pro Lys Phe Arg Glu Leu Ile Ile Glu Phe Ser
        35                  40                  45

Lys Met Ala Arg Asp Pro Gln Arg Tyr Leu Val Ile
    50                  55                  60
```

<210> SEQ ID NO 34
<211> LENGTH: 59
<212> TYPE: PRT
<213> ORGANISM: Artificial Sequence
<220> FEATURE:
<223> OTHER INFORMATION: peptide characterizing 1:28 mutant

<400> SEQUENCE: 34

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Glu Tyr Ile
            20                  25                  30

Asn Gln Ser Val Pro Lys Arg Pro Ala Gly Ser Val Gln Asn Pro Val
        35                  40                  45

Tyr His Asn Gln Pro Leu Asn Pro Ala Pro Ser
    50                  55
```

<210> SEQ ID NO 35
<211> LENGTH: 8
<212> TYPE: PRT
<213> ORGANISM: Artificial Sequence
<220> FEATURE:
<223> OTHER INFORMATION: peptide characterizing mLEEK
<220> FEATURE:

```
<221> NAME/KEY: misc_feature
<222> LOCATION: (5)..(5)
<223> OTHER INFORMATION: Xaa can be any naturally occurring amino acid

<400> SEQUENCE: 35

Glu Glu Lys Lys Xaa Val Thr Val
1               5

<210> SEQ ID NO 36
<211> LENGTH: 5
<212> TYPE: PRT
<213> ORGANISM: Artificial Sequence
<220> FEATURE:
<223> OTHER INFORMATION: peptide characterizing mLEEK
<220> FEATURE:
<221> NAME/KEY: misc_feature
<222> LOCATION: (3)..(3)
<223> OTHER INFORMATION: Xaa can be any naturally occurring amino acid

<400> SEQUENCE: 36

Lys Lys Xaa Val Thr
1               5

<210> SEQ ID NO 37
<211> LENGTH: 5
<212> TYPE: PRT
<213> ORGANISM: Artificial Sequence
<220> FEATURE:
<223> OTHER INFORMATION: peptide characterizing 1:28 mutant

<400> SEQUENCE: 37

Lys Lys Glu Tyr Ile
1               5

<210> SEQ ID NO 38
<211> LENGTH: 5
<212> TYPE: PRT
<213> ORGANISM: Artificial Sequence
<220> FEATURE:
<223> OTHER INFORMATION: peptide characterizing 1:24 mutant
<220> FEATURE:
<221> NAME/KEY: misc_feature
<222> LOCATION: (3)..(3)
<223> OTHER INFORMATION: Xaa can be any naturally occurring amino acid

<400> SEQUENCE: 38

Lys Lys Xaa Trp Met
1               5
```